United States Patent [19]

Brown et al.

[11] Patent Number: 5,576,334

[45] Date of Patent: Nov. 19, 1996

[54] ACYLUREA DERIVATIVES

[75] Inventors: George R. Brown, Wilmslow; Richard E. Shute, Macclesfield, both of United Kingdom

[73] Assignee: Zeneca Limited, London, United Kingdom

[21] Appl. No.: 266,462

[22] Filed: Jun. 27, 1994

[30] Foreign Application Priority Data

Jun. 28, 1993 [GB] United Kingdom .................. 9313268

[51] Int. Cl.$^6$ ...................... A61K 31/235; A61K 31/17; C07D 211/92; C07D 225/00
[52] U.S. Cl. .................. 514/317; 514/318; 514/327; 514/329; 514/353; 514/357; 514/535; 514/363; 514/595; 546/192; 546/193; 546/215; 546/216; 546/223; 546/224; 546/229; 546/231; 560/34; 562/439; 564/44
[58] Field of Search .................... 514/353, 357, 514/317, 318, 327, 329, 331, 335, 503, 598; 546/224, 192, 193, 215, 216, 223, 229, 231; 564/44; 560/34; 562/439

[56] References Cited

U.S. PATENT DOCUMENTS

| 5,039,805 | 8/1991 | Alig et al. | 546/224 |
| 5,084,466 | 1/1992 | Alig et al. | 514/353 |
| 5,227,490 | 7/1993 | Hartman et al. | 514/317 |
| 5,254,573 | 10/1993 | Bovy et al. | 514/357 |
| 5,264,420 | 11/1993 | Duggan et al. | 514/19 |
| 5,276,049 | 1/1994 | Himmelsbach et al. | 514/392 |
| 5,281,585 | 1/1994 | Duggan et al. | 514/79 |

FOREIGN PATENT DOCUMENTS

| 74101 | 10/1991 | Australia . |
| 10403 | 7/1992 | Australia . |
| 20569 | 1/1993 | Australia . |
| 21119 | 2/1993 | Australia . |
| 20892 | 3/1993 | Australia . |
| 27062 | 4/1993 | Australia . |
| 41201 | 12/1993 | Australia . |
| 2008116 | 9/1990 | Canada . |
| 2037153 | 9/1991 | Canada . |
| 2061661 | 9/1992 | Canada . |
| 2093770 | 10/1993 | Canada . |
| 2094773 | 10/1993 | Canada . |
| 0007648 | 6/1980 | European Pat. Off. . |
| 0116729 | 8/1984 | European Pat. Off. . |
| 0136745 | 10/1985 | European Pat. Off. . |
| 0475506 | 3/1992 | European Pat. Off. . |
| 0478328 | 4/1992 | European Pat. Off. . |
| 0479481 | 4/1992 | European Pat. Off. . |
| 0478363 | 4/1992 | European Pat. Off. . |
| 0478362 | 4/1992 | European Pat. Off. . |
| 0512829 | 11/1992 | European Pat. Off. . |
| 0512831 | 11/1992 | European Pat. Off. . |
| 0513675 | 11/1992 | European Pat. Off. . |
| 0529858 | 3/1993 | European Pat. Off. . |
| 0539343 | 4/1993 | European Pat. Off. . |
| 0540334 | 5/1993 | European Pat. Off. . |
| 0560730 | 9/1993 | European Pat. Off. . |
| 05562 | 5/1991 | WIPO . |
| 13552 | 8/1992 | WIPO . |
| 17196 | 10/1992 | WIPO . |
| 18117 | 10/1992 | WIPO . |
| 07867 | 4/1993 | WIPO . |
| 08181 | 4/1993 | WIPO . |
| 08174 | 4/1993 | WIPO . |
| 10091 | 5/1993 | WIPO . |
| 12074 | 6/1993 | WIPO . |
| 14077 | 7/1993 | WIPO . |
| 16038 | 8/1993 | WIPO . |
| 19046 | 9/1993 | WIPO . |
| 22303 | 11/1993 | WIPO . |
| 01396 | 1/1994 | WIPO . |

OTHER PUBLICATIONS

Alig, et al., "Low Molecular Weight, Non–peptide Fibrinogen Receptor Antagonists", J. Med. Chem., 1992, 35, 4393–4407.

Hartman, et al., "Non–peptide Fibrinogen Receptor Antagonists 1. Discovery and Design of Exosite Inhibitors", J. Med. Chem., 1992, 35, 4640–4642.

Primary Examiner—C. Warren Ivy
Assistant Examiner—Raymond Compton
Attorney, Agent, or Firm—Cushman Darby & Cushman, L.L.P.

[57] ABSTRACT

The invention concerns chemical compounds of formula I

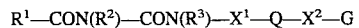

$$R^1\text{—CON}(R^2)\text{—CON}(R^3)\text{—}X^1\text{—Q—}X^2\text{—G} \qquad \text{I}$$

and pharmaceutically acceptable metabolically labile esters or amides thereof, and pharmaceutically acceptable salts thereof, in which $R^1$, $R^2$, $R^3$, $X^1$, Q, $X^2$ and G have the meanings given in the specification. The invention concerns processes for the preparation of the chemical compounds of formula I, pharmaceutical compositions containing them and their use as inhibitors of the binding of fibrinogen to glycoprotein IIb/IIIa.

11 Claims, No Drawings

ACYLUREA DERIVATIVES

The present invention relates to a group of chemical compounds which inhibit cell adhesion (for example, platelet aggregation), to processes for their preparation and to pharmaceutical compositions containing them.

A variety of diseases involve cell adhesion during their development. For example, platelet aggregation is involved in the formation of blood thrombi, which can lead to diseases such as thrombosis, (for example stroke and thrombotic events accompanying unstable angina and transient ischaemic attack), myocardial infarction, atherosclerosis, thromboembolism and reocclusion during and after thrombolytic therapy.

It is widely believed that the platelet membrane glycoprotein IIb-IIIa (GPIIb-IIIa) mediates platelet aggregation. Adhesion molecules such as fibrinogen and von Willebrand Factor are believed to bind to GPIIb-IIIa sites on adjacent platelets and thereby cause them to aggregate. Other adhesion molecules which are known to bind to GPIIb-IIIa are fibronectin, vitronectin and thrombospondin.

Compounds which inhibit platelet aggregation and the binding of adhesion molecules to GPIIb-IIIa are known, for example from U.S. Pat. No. 5,039,805 and 5,084,446, Canadian patent applications numbers 2,008,161, 2,037,153 and 2,061,661, and Alig et al., J. Med. Chem., 1992, 35, 4393–4407. Commonly the structures of these compounds are based upon the binding regions of the adhesion molecules, which are peptides. For example, a portion of fibrinogen which is believed to bind to GPIIb-IIIa is the amino acid sequence RGD (arginyl glycyl aspartate).

The ability to inhibit platelet aggregation and to inhibit the binding of fibrinogen to GPIIb-IIIa has now been found to be possessed by certain acid derivatives containing an acylureido group.

According to one aspect, therefore, the present invention provides a compound of the general formula I (formula set out at the end of the description together with the other formulae referred to herein by Roman numerals) wherein $R^1$ represents a group of formula II or III in which A is attached meta or para to the position where the group $CONR^2CONR^3$ is attached and is selected from aminomethyl, guanidino and $R^aN=C(NH_2)$— where $R^a$ is hydrogen or phenyl which is unsubstituted or substituted by 1 or 2 of halogeno, (1–4C)alkyl, (1–4C)alkoxy, cyano and nitro, E is CH or N, $Z^1$ is hydrogen, halogeno, (1–4C)alkyl, (1–4C)alkoxy, cyano or nitro, T is N or CH and $X^3$ is a bond, (1–4C)alkylene or, when T is CH, oxy(1–3C)alkylene;

$R^2$ and $R^3$ which may be the same or different represent hydrogen (1–4C)alkyl or ar(1–4C)alkyl;

$X^1$ is a bond or (1–4C)alkylene, provided that when Q is a group of formula V, $X^1$ is not methylene;

Q is a group of formula IV or V in which $Z^2$ is hydrogen, halogeno, (1–4C)alkyl, (1–4C)alkoxy, cyano or nitro, and $Z^3$ is a group of formula $X^2$—$G^a$ in which $X^2$ can have any of the values given hereinafter for $X^2$ and $G^a$ can have any of the values given hereinafter for G, or $G^a$ has any of the values given hereinbefore for $Z^2$;

or the partial structure of formula $NR^3X^1Q$ is a group of formula V in which $Z^3$ can have any of the values given hereinbefore for $Z^3$;

$X^2$ is a bond, (1–4C)alkylene, oxy(1–3C)alkylene, (1–3C)alkylene-oxy(1–3C)alkylene or a group of formula $CH_2CH(NHXR^4)$ in which X is $SO_2$, CO or $CO_2$ and $R^4$ is (1–6C)alkyl, (6–12C)aryl or (6–12C)aryl(1–4C)alkyl in which any aryl group is optionally substituted by (1–4C)alkyl, or $X^2$ is a group of formula $CH_2CH(CH_2CH_2O(1–4C)alkyl)$; and G is a carboxy group or a pharmaceutically acceptable metabolically labile ester or amide thereof; and pharmaceutically acceptable salts thereof.

It will be appreciated that depending on the nature of the substituents, in containing one or more chiral centres, the formula I compounds may exist in and be isolated in one or more different enantiomeric or racemic forms (or a mixture thereof). It is to be understood that the invention includes any of such forms which possesses the property of inhibiting platelet aggregation and inhibiting the binding of fibrinogen to GpIIb-IIIa, it being well known how to prepare individual enantiomeric forms, for example, by synthesis from appropriate chiral starting materials or by resolution of a racemic form. Similarly, the biological properties of a particular form may be readily evaluated, for example by use of one or more of the standard in vitro or ex vivo screening tests detailed hereinbelow.

It will also be appreciated that compounds of formula I wherein $R^1$ represents a group of formula II and A represents the group $R^aN=C(NH_2)$— may exist in tautomeric forms, and that the invention includes the compounds in any of their tautomeric forms.

A is preferably a group of formula $R^aN=C(NH_2)$—. It is preferably attached para to the position where the group $CONR^2CONR^3$ is attached.

Examples of values for $R^a$ include hydrogen and phenyl. Examples of substituents on $R^a$ when it is phenyl include fluoro, chloro, bromo, methyl, ethyl, methoxy, ethoxy, cyano and nitro.

When $R^1$ represents a group of formula II bearing the substituent $Z^1$, $Z^1$ may represent, for example, hydrogen, fluoro, chloro, bromo, methyl, ethyl, methoxy, ethoxy, cyano or nitro.

When $R^1$ represents a group of formula III, examples of values for $X^3$ include a bond, methylene, ethylene, trimethylene and, when T is CH, oxymethylene.

Examples of values for $R^1$ include 3-aminomethylphenyl, 4-aminomethylphenyl, 4-amidinophenyl, 4-($N^2$-phenyl)amidinophenyl, 6-amidinopyrid-3-yl, 5-amidinopyrid-2-yl, piperidin-4-yl, piperidin-4-ylmethyl, 2-piperidin-4-ylethyl, piperidin-4-yloxymethyl and piperazin-1-yl.

A (1–4C)alkyl group represented by $R^2$ or $R^3$ may be, for example, methyl or ethyl. An ar(1–4C)alkyl may be, for example, benzyl. Preferably one of $R^2$ and $R^3$ is hydrogen and the other is hydrogen, methyl or benzyl. More preferably each of $R^2$ and $R^3$ represents hydrogen.

Examples of values for $X^1$ when it represents (1–4C)alkylene are methylene and ethylene. Preferably X represents a bond when Q represents a group of formula IV, and a (2–4C)alkylene group when Q represents a group of formula V.

In the group Q, when it is a group of formula IV, examples of values for $Z^2$ include hydrogen, fluoro, chloro, bromo, methyl, ethyl, methoxy, ethoxy, cyano and nitro. Hydrogen is a preferred value for $Z^2$.

In the group Q, when it is a group of formula IV or V, and $Z^3$ is a group of formula $X^2$—$G^a$, examples of values for $X^2$ include a bond, methylene, ethylene, trimethylene, oxymethylene, oxyethylene, methyleneoxymethylene, groups of formula $CH_2CH(NHXR^4)$ in which X is $SO_2$, CO or $CO_2$ and $R^4$ is methyl, ethyl, propyl, butyl, pentyl, phenyl, tolyl or benzyl, and groups of formula $CH_2CH(CH_2CH_2O(1-4C)alkyl)$ in which the (1–4C)alkyl group is methyl, ethyl or propyl, and examples of values for $G^a$ include carboxy (or a pharmaceutically acceptable metabolically labile ester or amide thereof), hydrogen, fluoro, chloro, bromo, methyl, ethyl, methoxy, ethoxy, cyano and nitro. Preferably $Z^3$ is hydrogen or a group of formula $X^2$—$G^a$ in which $X^2$ is oxymethylene and $G^a$ is carboxy or a (1–6C)alkyl ester thereof such as the methyl, ethyl and t-butyl ester.

In the partial structure of formula $NR^3X^1Q$ when it is a group of formula V in which $Z^3$ is a group of formula $X^2$—$G^a$, each of $X^2$ and $G^a$ may have any of the values given therefor in the preceding paragraph.

Examples of values for $X^2$ include a bond, methylene, ethylene, trimethylene, oxymethylene, oxyethylene, methyleneoxymethylene, groups of formula $CH_2CH(NHXR^4)$ in which X is $SO_2$, CO or $CO_2$ and $R^4$ is methyl, ethyl, propyl, butyl, pentyl, phenyl, tolyl or benzyl, and groups of formula $CH_2CH(CH_2CH_2O(1-4C)alkyl)$ in which the (1–4C)alkyl group is methyl, ethyl or propyl. Preferably $X^2$ is oxymethylene, methyleneoxymethylene, a group of formula $CH_2CH(NHSO_2(CH_2)_3CH_3)$ or a group of formula $CH_2CH(CH_2CH_2OCH_2CH_3)$.

Examples of ester derivatives of a carboxy group represented by G include esters formed with alcohols such as (1–6C)alkanols, for example methanol, ethanol, propanol and t-butanol; indanol; adamantol; (1–6C)alkanoyloxy(1–4C)alkanols such as pivaloyloxymethanol; glycolamides; (5-methyl-2-oxo-1,3-dioxol-4-yl)methyl alcohol; and (1–4C)alkoxycarbonyl(1–4C)alkanols.

Examples of amide derivatives of a carboxy group represented by G include amides derived from ammonia and amines such as (1–4C)alkylamines, for example methylamine; di(1–4C)alkylamines, for example dimethylamine, (1–4C)alkoxy(1–4C)alkylamines such as methoxyethylamine; and amino acids such as glycine or an ester thereof.

Preferably G represents a carboxy group or a (1–4C)alkoxycarbonyl group such as methoxycarbonyl, ethoxycarbonyl, propoxycarbonyl, isopropoxycarbonyl or t-butoxycarbonyl.

Particular pharmaceutically acceptable salts include, for example, salts with acids affording physiologically acceptable anions, such as salts with mineral acids, for example a hydrogen halide (such as hydrogen chloride and hydrogen bromide), sulphuric acid or phosphoric acid, and salts with organic acids, for example acetic acid and trifluoroacetic acid. Other pharmaceutically acceptable salts include, for example salts with inorganic bases such as alkali metal and alkaline earth metal salts (for example sodium salts), ammonium salts, and salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Particular compounds of the invention include, for example, a chemical compound of formula I wherein $R^1$ represents a group of formula II or III in which A is attached meta or para to the position where the group $CONR^2CONR^3$ is attached and is selected from aminomethyl, guanidino and $R^aN=C(NH_2)$— where $R^a$ is hydrogen or phenyl which is unsubstituted or substituted by 1 or 2 of halogeno, (1–4C)alkyl, (1–4C)alkoxy, cyano and nitro, E is CH or N, $Z^1$ is hydrogen, halogeno, (1–4C)alkyl, (1–4C)alkoxy, cyano or nitro, T is N or CH, and $X^3$ is a bond, (1–4C)alkylene or, when T is CH, oxy(1–3C)alkylene;

$R^2$ and $R^3$, which may be the same or different, represent hydrogen, (1–4C)alkyl or ar(1–4C)alkyl;

$X^1$ is a bond or (1–4C)alkylene, provided that when Q is a group of formula V, $X^1$ is not methylene;

Q is a group of formula IV or V in which $Z^2$ is hydrogen, halogeno, (1–4C)alkyl, (1–4C)alkoxy, cyano or nitro, and $Z^3$ is a group of formula $X^2$—$G^a$ in which $G^a$ can have any of the values given for G, or has any of the values given for $Z^2$;

$X^2$ is a bond, (1–4C)alkylene, oxy(1–3C)alkylene or a group of formula $CH_2CH(NHXR^4)$ in which X is $SO_2$, CO or $CO_2$ and $R^4$ is (1–6C)alkyl, (6–12C)aryl or (6–12C)aryl(1–4C)alkyl in which any aryl group is optionally substituted by (1–4C)alkyl; and G is a carboxy group or a pharmaceutically acceptable metabolically labile ester or amide thereof; and pharmaceutically acceptable salts thereof.

Further particular compounds of the invention include, for example, chemical compounds of formula I, or pharmaceutically acceptable salts thereof, in which, unless otherwise stated, each of the variable groups $R^1$, $R^2$, $R^3$, $X^1$, Q, $X^2$ and G have any of the meanings defined hereinbefore or in this section concerning further particular compounds of the invention:

(a) $R^1$ represents a group of formula II in which A is attached para to the position where the group $CONR^2CONR^3$ is attached and is selected from aminomethyl, guanidino and $R^aN=C(NH_2)$— where $R^a$ is hydrogen or phenyl, E is CH or N, and $Z^1$ is hydrogen, fluoro, chloro, methyl, methoxy or cyano;

(b) $R^1$ represents a group of formula III in which T is CH or N, and $X^3$ is a bond, methylene, ethylene, trimethylene or, when T is CH, oxymethylene;

(c) $R^2$ and $R^3$, which may be the same or different, represent hydrogen, methyl, ethyl or benzyl;

(d) $X^1$ is a bond;

(e) Q is a group of formula IV in which $Z^2$ is hydrogen, fluoro, chloro, methyl, methoxy or cyano, and $Z^3$ is hydrogen or a group of formula $X^2$—$G^a$ in which $X^2$ is methylene, ethylene or oxymethylene and $G^a$ is a carboxy group or a pharmaceutically acceptable metabolically labile ester thereof;

(f) Q is a group of formula V in which $Z^3$ is hydrogen or a group of formula $X^2$—$G^a$ in which $X^2$ is methylene, ethylene or oxymethylene and $G^a$ is a carboxy group or a pharmaceutically acceptable metabolically labile ester thereof;

(g) the partial structure of formula $NR^3X^1Q$ is a group of formula V in which $Z^3$ is hydrogen or a group of formula $X^2$—$G^a$ in which $X^2$ is methylene, ethylene or oxymethylene and $G^a$ is a carboxy group or a pharmaceutically acceptable metabolically labile ester thereof;

(h) $X^2$ is methylene, ethylene, trimethylene, oxymethylene or methyleneoxymethylene;

(i) $X^2$ is a group of formula $CH_2CH(NHXR^4)$ in which X is $SO_2$ and $R^4$ is methyl, ethyl, propyl, butyl or pentyl, or $X^2$ is a group of formula CH₂CH(CH₂CH₂O(1–4C)alkyl) in which the (1–4C)alkyl group is methyl, ethyl or propyl; and (j) G is a carboxy group or a pharmaceutically acceptable metabolically labile ester thereof.

A preferred compound of the invention is a chemical compound of formula I wherein $R^1$ represents a group of formula II in which A is attached para to the position where the group $CONR^2CONR^3$ is attached and is selected from aminomethyl and a group of formula $R^aN=C(NH_2)-$ where $R^a$ is hydrogen or phenyl, E is CH or N and $Z^1$ is hydrogen, fluoro, chloro, methyl or methoxy;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula $X^2-G^a$ in which $X^2$ is oxymethylene and $G^a$ is carboxy, methoxycarbonyl, ethoxycarbonyl, propoxycarbonyl, isopropoxycarbonyl or t-butoxycarbonyl;

$X^2$ is ethylene, trimethylene, oxymethylene, methyleneoxymethylene, a group of formula $CH_2CH(NHSO_2(CH_2)_3CH_3)$ or a group of formula $CH_2CH(CH_2CH_2OCH_2CH_3)$; and G is carboxy, methoxycarbonyl, ethoxycarbonyl, propoxycarbonyl, isopropoxycarbonyl or t-butoxycarbonyl;

or a pharmaceutically-acceptable salt thereof.

A further preferred compound of the invention is a chemical compound of formula I wherein $R^1$ represents a group of formula III in which T is CH or N, and $X^3$ is a bond, methylene, ethylene or, when T is CH, oxymethylene;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula $X^2-G^a$ in which $X^2$ is oxymethylene and $G^a$ is carboxy, methoxycarbonyl, ethoxycarbonyl, propoxycarbonyl, isopropoxycarbonyl or t-butoxycarbonyl;

$X^2$ is ethylene, trimethylene, oxymethylene or methyleneoxymethylene; and

G is carboxy, methoxycarbonyl, ethoxycarbonyl, propoxycarbonyl, isopropoxycarbonyl or t-butoxycarbonyl;

or a pharmaceutically acceptable salt thereof.

A further preferred compound of the invention is a chemical compound of formula I wherein $R^1$ represents a group of formula II in which A is attached para to the position where the group $CONR^2$ is attached and is selected from aminomethyl and a group of formula $R^aN=C(NH_2)-$ where $R^a$ is hydrogen or phenyl, E is CH or N and $Z^1$ is hydrogen, fluoro, chloro, methyl or methoxy;

$R^2$ is hydrogen, methyl or benzyl;

the partial structure of formula $NR^3X^1Q$ is a group of formula V in which $Z^3$ is hydrogen or a group of formula $X^2-G^a$ in which $X^2$ is oxymethylene and $G^a$ is carboxy, methoxycarbonyl, ethoxycarbonyl, propoxycarbonyl, isopropoxycarbonyl or t-butoxycarbonyl;

$X^2$ is ethylene, trimethylene, oxymethylene or methyleneoxymethylene; and

G is carboxy, methoxycarbonyl, ethoxycarbonyl, propoxycarbonyl, isopropoxycarbonyl or t-butoxycarbonyl;

or a pharmaceutically acceptable salt thereof.

A further preferred compound of the invention is a chemical compound of formula I wherein $R^1$ represents a group of formula II in which A is attached para to the position where the group $CONR^2CONR^3$ is attached and is a group of formula $R^aN=C(NH_2)-$ where $R^a$ is hydrogen, E is CH and $Z^1$ is hydrogen;

$R^2$ is hydrogen;

$R^3$ is hydrogen or methyl;

$X^1$ is a bond;

Q is a group of formula IV in which $Z^2$ is hydrogen, fluoro, chloro or methyl, and $Z^3$ is hydrogen or a group of formula $X^2-G^a$ in which $X^2$ is oxymethylene and $G^a$ is carboxy, methoxycarbonyl, ethoxycarbonyl, propoxycarbonyl, isopropoxycarbonyl or t-butoxycarbonyl;

$X^2$ is oxymethylene; and

G is carboxy, methoxycarbonyl, ethoxycarbonyl, propoxycarbonyl, isopropoxycarbonyl or t-butoxycarbonyl;

or a pharmaceutically acceptable salt thereof.

A further preferred compound of the invention is a chemical compound of formula I wherein $R^1$ represents a group of formula III in which T is CH and $X^3$ is ethylene;

$R^2$ is hydrogen;

$R^3$ is hydrogen or methyl;

X is a bond;

Q is a group of formula IV in which $Z^2$ is hydrogen, fluoro, chloro or methyl, and $Z^3$ is hydrogen;

$X^2$ is oxymethylene; and

G is carboxy, methoxycarbonyl, ethoxycarbonyl, propoxycarbonyl, isopropoxycarbonyl or t-butoxycarbonyl;

or a pharmaceutically acceptable salt thereof.

A further preferred compound of the invention is a chemical compound of formula I wherein $R^1$ represents a group of formula II in which A is attached para to the position where the group $CONR^2$ is attached and is a group of formula $R^aN=C(NH_2)-$ where $R^a$ is hydrogen, E is CH and $Z^1$ is hydrogen;

$R^2$ is hydrogen;

the partial structure of formula $NR^3X^1Q$ is a group of formula V in which $Z^3$ is hydrogen;

$X^2$ is oxymethylene or methyleneoxymethylene; and

G is carboxy, methoxycarbonyl, ethoxycarbonyl, propoxycarbonyl, isopropoxycarbonyl or t-butoxycarbonyl;

or a pharmaceutically acceptable salt thereof.

Specific especially preferred compounds of the invention include chemical compounds of formula I selected from:

methyl 4-[3-(4-amidinobenzoyl)ureido]phenoxyacetate, t-butyl 4-[3-(4-amidinobenzoyl)ureido]phenoxyacetate, 4-[3-(4-amidinobenzoyl)ureido]phenoxyacetic acid, ethyl 4-[3-(4-amidinobenzoyl)ureido]phenoxyacetate, isopropyl 4-[3-(4-amidinobenzoyl)ureido]phenoxyacetate, N-[N-(4-amidinobenzoyl)carbamoyl]piperidin-4-yloxy-acetic acid and N-[N-(4-amidinobenzoyl)carbamoyl]piperidin-4-yl-methoxyacetic acid; or a pharmaceutically acceptable salt thereof.

The compounds of formula I, the metabolically labile esters and amides thereof, and the pharmaceutically acceptable salts thereof may be prepared by procedures analogous to procedures known in the art for the preparation of structurally analogous compounds. Such procedures are included as a further feature of the invention and include the following preferred procedures for the manufacture of a compound of the formula I in which $R^1$, $R^2$, $R^3$, $X^1$, Q, $X^2$ and G have any of the meanings defined above:

(A) For a compound of formula I in which G is carboxy, deprotecting a compound of formula VI in which $G^1$ is a carboxy protecting group.

$G^1$ may be any conventional carboxyl protecting group that may be removed without interfering with other parts of the molecule. Examples of carboxy protecting groups include (1–6C)alkyl groups (such as methyl, ethyl, propyl or t-butyl), phenyl and benzyl, the phenyl moiety in any of which may optionally bear 1 or 2 of halogeno, (1–4C)alkyl, (1–4C)alkoxy or nitro.

The deprotection may be carried out using any one or more of the conventional reagents and conditions known in the art for converting carboxylic esters into carboxylic acids. Thus, for example, the deprotection may conveniently be performed by base catalysed hydrolysis, for example by using an alkali metal hydroxide such as lithium, potassium or sodium hydroxide, or a tertiary amine such as triethylamine, in the presence of water. The base catalysed hydrolysis may conveniently be performed in the presence of a solvent such as an alcohol, for example methanol or ethanol, or an ether such as tetrahydrofuran or dioxan. Alternatively the deprotection may be carried out by acid catalysed hydrolysis, for example using acetic acid or trifluoroacetic acid. Suitable solvents for the acid catalysed hydrolysis include alcohols such as those mentioned above, halogenated hydrocarbons such as dichloromethane, ethers such as anisole, and water. The temperature is conveniently in the range of from –10° to 100° C., for example from 10° to 50° C. When the alcohol residue is t-butyl, this may also conveniently be removed by heating, for example at a temperature in the range of from 80° to 150° C., alone or in the presence of a suitable diluent such as diphenyl ether or diphenyl sulphone.

It will be appreciated that a compound of formula I in which G represents carboxy and Q represents a group of formula IV or V wherein $Z^3$ represents a group of formula $X^2$-COOH may be prepared by this process starting from a compound of formula VI in which Q represents a group of formula IV or V and $Z^3$ represents a group of formula $X^2$—COOH or $X^2$—$COOG^1$.

(B) For a compound of formula I in which $R^1$ is a group of formula II and A is an aminomethyl or amidino group, deprotecting a compound of formula VII in which A is a protected aminomethyl or amidino group.

$A^1$ may be any conventional aminomethyl or amidino protecting group that may be deprotected without interfering with other parts of the molecule. Examples of protecting groups include oxycarbonyl groups such as t-butoxycarbonyl and benzyloxycarbonyl.

The deprotection may be carried out using any one or more of the conventional reagents and conditions known in the art for removing amine protecting groups. A t-butoxycarbonyl group may be removed by hydrolysis, for example by acid catalysed hydrolysis using an acid such as trifluoroacetic acid. Suitable solvents include halogenated hydrocarbons such as dichloromethane. A benzyloxycarbonyl group may conveniently be removed, for example, by hydrogenation in the presence of a palladium catalyst such as palladium on charcoal. The temperature is conveniently in the range of from –10° to 100° C., for example from 10° to 50° C.

In some cases the reaction conditions required to perform process (A) are the same as those required to perform process (B). In such cases it is possible to perform processes (A) and (B) at the same time by starting with a compound having an appropriate carboxyl protecting group and an appropriately protected aminomethyl or amidino group. Such a compound is represented by the formula VIII.

(C) For a compound of formula I in which $R^2$ and $R^3$ represent hydrogen atoms, reacting an isocyanate of formula IX with an amine of formula X.

Suitable solvents include halogenated hydrocarbons such as dichloromethane and nitriles such as acetonitrile. The reaction is conveniently performed at a temperature in the range of from –10° to 100° C.

(D) For a compound of formula I in which $X^2$ is a group of formula $CH_2CH(NHXR^4)$, reacting a compound of formula XI in which $X^{2a}$ is $CH_2CH(NH_2)$, or an acid addition salt thereof, with a compound of formula XII in which $U^1$ is a leaving atom or group.

Examples of values for $U^1$ include halogen such as chlorine or bromine and hydrocarbylsulphonyloxy such as methanesulphonyloxy and p-toluenesulphonyloxy. Examples of acid addition salts include for example, the hydrochloride. The reaction may conveniently be effected at a temperature in the range of from –10° to 120° C. preferably from 10° to 100° C. Suitable solvents include for example ethers such as tetrahydrofuran, amides such as dimethylformamide, nitriles such as acetonitrile, halogenated hydrocarbons such as dichloromethane and alcohols such as ethanol. The reaction is conveniently performed in the presence of a base, for example a tertiary amine such as triethylamine.

(E) For a compound of formula I in which $R^1$ is a group of formula II and A is a group of formula $R^aN=C(NH_2)$—, reacting a compound of formula XIII, in which $U^2$ is a leaving atom or group, with a compound of formula $R^aNH_2$, or an acid addition salt thereof.

Examples of values for $U^2$ include (1–4C)alkylthio groups such as methylthio. Suitable media for the reaction include alcohols such as methanol or ethanol, and halogenated hydrocarbons such as dichloromethane. The reaction is conveniently performed at a temperature in the range of from –10° to 100° C. An acid addition salt of a compound of formula $R^aNH_2$ may be for example, an addition salt of an organic acid such as acetic acid or an inorganic acid such as hydrochloric acid.

The intermediates used in the aforementioned processes are either known or may be prepared by methods analogous to methods known for preparing known compounds. In general, the intermediates containing an acylureido group may be prepared by reacting the appropriate isocyanate derivative with the appropriate amine.

Thus, the compounds of formula VI in which $R^2$ and $R^3$ represent hydrogen may be prepared by reacting an isocyanate of formula IX with an amine of formula XIV by a method analogous to that of process (C) described hereinabove.

The compounds of formula VI in which $R^1$ is a group of formula II and A is an aminomethyl group may also be prepared by selectively deprotecting a compound of formula VIII. Similarily, the compounds of formula VII may also be prepared by selectively deprotecting a compound of formula VIII.

The compounds of formula VIII in which $R^2$ and $R^3$ represent hydrogen may be prepared by reacting an isocyanate of formula XV with an amine of formula XIV following a method analogous to that of process (C) described hereinabove.

The compounds of formula IX and XV may be prepared respectively by reacting a compound of formula XVI or XVII with oxalyl chloride. The reaction is conveniently effected at a temperature in the range of from −10° to 100° C. Suitable solvents include halogenated hydrocarbons such as dichloromethane and nitriles such as acetonitrile.

The compounds of formula XI in which $R^2$ and $R^3$ are hydrogen may be prepared by a method analagous to process (C), by reacting an isocyanate of formula IX with an amine of formula XVIII, or a protected derivative thereof, followed if necessary by removal of the protecting group(s).

The compounds of formula XIII in which $U^2$ is a (1–4C)alkylthio group may be prepared by reacting a compound of formula XIX with an alkylating agent, for example a (1–4C)alkyl halide such as methyl iodide. Suitable media for the reaction include ketones such as acetone. Conveniently the reaction may be performed at a temperature in the range of from 0° to 100° C.

The compounds of formula XIX may be prepared by reacting a compound of formula XX with hydrogen sulphide. The reaction is conveniently effected in the presence of a base such as triethylamine and in the presence of a solvent such as pyridine.

The compounds of formula XX in which $R^2$ and $R^3$ are hydrogen may be prepared by reacting an isocyanate of formula XXI with an amine of formula X. Suitable solvents for the reaction include nitriles such as acetonitrile.

The compounds of formula XXI may be prepared by reacting a compound of formula XXII with oxalyl chloride. Suitable solvents include halogenated hydrocarbons such as 1,2-dichloroethane.

The compounds of formula I may be converted into pharmaceutically acceptable salts and/or metabolically labile esters or amides thereof by methods well known in the art. For example, a pharmaceutically acceptable salt may be formed by reacting a compound of formula I with an acid capable of affording a physiologically acceptable anion, or a base capable of affording a physiologically acceptable cation. A pharmaceutically acceptable metabolically labile ester or amide may be formed respectively by esterifying a compound of formula I using a conventional technique, or by reacting an acid, or a reactive derivative thereof, with an appropriate amine. Similarly, when an optically active form of a chiral compound of formula I is required, either one of processes (A)–(E) above may be carried out using the appropriate optically active starting material or else a racemic form may be resolved by a conventional procedure, for example, using an optically active form of a suitable acid.

A suitable reactive derivative of an acid may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol or an alcohol such as 1-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

Many of the intermediates, for example compounds of formulae VI, VII, VIII, XI, XIII, XIX and XX are novel and form further aspects of this invention.

The ability of the compounds of formula I to inhibit platelet aggregation may be demonstrated using a standard test (a) based on that described by Born (*Nature*, 1962, 194, 927–929) and involving:

(i) aggregating human, citrated, platelet-rich plasma by addition of adenosine diphosphate (ADP) so as to generate a dose-response curve;

(ii) generating a dose-response curve for ADP stimulated platelet aggregation in the presence of increasing amounts of a test compound (generally in the range $10^{-5}M$ to $10^{-10}M$); and (iii) calculating a $pA_2$ value indicating potency of platelet aggregation inhibition for the test compound, averaged over several concentrations, from the calculated 50% response value for ADP aggregation in the presence and absence of the test compound.

Test (a) may be modified so as to assess the effects of a test compound ex vivo on the aggregation of human blood platelets after administration of the test compound to a laboratory animal, such as a rat, rabbit, guinea pig, mouse or dog. For example, groups of four male, fasted Alderley Park Wistar rats are orally dosed with a test compound or appropriate vehicle, and at suitable time intervals (1, 3, 5 and 8 hours after dosing) animals are anaesthetised with fluothane and bled by heart puncture. Blood is collected into 3.2% citrate (1 part to 9 parts whole blood) and platelet poor plasma (ppp) prepared by centrifugation (4500×g for 10 minutes).

Human blood is collected into 3.2% trisodium citrate (1 part to 9 parts whole blood) and centrifugated (200×g for 15 minutes) to produce platelet rich plasma (prp).

Equal volumes (125 µl) of rat ppp and human prp are mixed together, ADP added, and the whole incubated (37° C.) and stirred (900 rpm) in a BioData platelet aggregometer. Aggregation is induced with ADP and agonist $EC_{50}$ values calculated for human prp/rat ppp mixtures from animals dosed with test compound or vehicle. A mean concentration ratio (concentration of ADP required to cause a 50% aggregation response in human prp/rat ppp mixtures from animals dosed with antagonist, divided by the concentration of ADP to cause 50% aggregation in human prp/rat ppp mixtures from animals dosed with vehicle) is calculated at each time point.

The ability of the compounds of formula I to inhibit binding of fibrinogen to GPIIb-IIIa may be demonstrated using the following standard test (b) involving:

(i) Preparation of human platelet lysates. Platelet rich plasma (PRP) is harvested by centrifugation (1000 rpm, 15 minutes) of whole blood anticoagulated with acid citrate dextrose (trisodium citrate 85 mM, citric acid 70 mM, d-glucose 110 mM) 1 part to 6 parts blood. Prostacyclin ($PGI_2$, 1 µM) is added to the PRP before centrifugation (2400 rpm, 15 mins) and the resulting pellet is resuspended in modified Tyrodes' solution (NACl 130 mM, KCl 26 mM, $NaHCO_3$ 12 mM, $NaH_2PO_4$ 0.5 mM, $MgCl_2$ 1 mM, $CaCl_2$ 20 mM, Glucose 12 mM, HEPES 5 mM) containing bovine serum albumin 3.5 g/L, $PGI_2$ 1 µM and hirudin 0.5 U/ml. The platelet suspension is centrifuged (2400 rpm, 15 minutes) and the resultant pellet resuspended in 500 µl of lysis buffer (octyl glucoside 50 mM, HEPES 10 mM, NaCl 150 mM, CaCl₂ 1 mM, MgCl₂ 1 mM, PMSF 1 mM, NEM 10 mM, leupeptin 0.1 mM), agitated at 4° C. for 15 minutes then centrifuged at 24000 rpm, 15 minutes. The supernatant is stored at 4° C. and the pellet re-suspended in 500 µl of lysis buffer. The centrifugation process is repeated a further 3 times, the pooled supernatants being stored at −70° C.

(ii) Receptor purification. Glycoprotein IIb/IIIa is isolated from human platelet lysates using a 2 ml peptide (KYGRGDS) coupled CNBr activated Sepharose affinity column. A 1.5 ml volume of platelet lysate is placed on the column and allowed to stand overnight at 4° C. Buffer (30 ml, octyl glucoside 25 mM, HEPES 10 mM, NaCl 150 mM, CaCl2 1 mM, MgCl2 1 mM, PMSF 1 mM, NEM 10 mM, leupeptin 0.1 mM) is passed through the column and 2 ml fractions are collected throughout. GPIIb/IIIa is eluted with 12 ml of buffer containing HHLGGAKQAGDV (2 mg/ml, pH7.5), the column is washed using 4 ml buffer and the remaining GPIIb/IIIa eluted using 12 ml buffer containing GRGD-SPG (1 mg/ml pH7.5). The column is finally washed using 20 ml of buffer and can be used for up to three such preparations. Fractions containing GPIIb/IIIa are identified using gel electrophoresis and immunoblotting, pooled and stored at −70° C.

(iii) GPIIb/IIIa ELISA 96 well microtitre plates are coated with 100 µl purified human platelet fibrinogen receptor (GPIIb/IIIa) diluted in coating buffer (Tris-HCl 20 mM, NaCl 150 mM, CaCl₂ 1 mM, pH7.4) and left overnight at 4° C. The plates are washed using washing buffer (Tris-HCl 50 mM, NaCl 100 mM, CaCl₂ 2 mM, pH7.4) and non-specific binding blocked by the addition of 200 µl 12% BSA (2 hours, 30° C.). The plates are washed prior to incubation (2 hours, 30° C.) with 100 µl biotinylated fibrinogen (10 nM) containing either vehicle or test compound. The plates are washed, incubated with streptavidin (5 µg/ml, 1 hour, ambient temperature), then washed again before the addition of 100 µl biotinylated horse radish peroxidase (0.1 µg/ml, 1 hour, ambient temperature). The plates are then washed and equal volumes of peroxidase substrate (3,3',5,5'-tetramethylbenzidine 0.4g/l) and H₂O₂ (0.02%) are mixed together immediately before addition of 150 µl to each well. Colour is allowed to develop for 10–15 minutes before optical densities are read at 650 nM.

| Abbreviations | |
|---|---|
| PMSF | Phenylmethylsulphonyl fluoride |
| HEPES | 2-[4-(2-hydroxyethyl)piperazin-1-yl]ethanesulphonic acid |
| NEM | N-ethylmaleimide |

The concentration of compound required to cause 50% inhibition of biotinylated fibrinogen binding is calculated and expressed as a $pIC_{50}$ ($-\log(IC_{50})$).

The compounds of formula I exemplified herein have been found to show effects in the following ranges in at least one of the above tests:

test (a): $pA_2$ of >4.5 test (b): $pIC_{50}$ of >4.5

In general, it has been found that compounds of formula I in which G is carboxy show a higher level of activity in test (a) and test (b) than those in which G is an ester group. However, the compounds in which G is an ester group in general have been found to show a higher level of activity than those where G is carboxy in test (a) when the test is modified to assess the activity of test compounds on oral administration For example, the methyl ester compound described in Example 1 hereinafter has been found to give a $pA_2$ of 7.6 in test (a) and a $pIC_{50}$ of 6.5 in test (b), whereas the carboxylic acid compound of Example 3 has been found to give a $pA_2$ of 8.4 in test (a) and a $pIC_{50}$ of 8.6 in test (b). However, the t-butyl ester compound of Example 2 has been found to be active for up to 8 hours when dosed orally to dogs at 1 mg/kg. Without wishing to be bound by theory it is accordingly believed that the compounds of formula I in which G represents an ester group function as a pro-drugs for compounds of formula I in which G is a carboxy group.

As stated previously, the compounds of formula I may be used in the therapy or prevention of diseases in which cell adhesion (especially platelet aggregation) is involved, for example venous or arterial thrombosis (for example pulmonary embolism, stroke and thrombotic events accompanying unstable angina and transient ischaemic attack), myocardial infarction, migraine, atherosclerosis, thromboembolism and reocclusion during and after thrombolytic therapy. The compounds may also be useful for the prevention of reocclusion or restenosis following percutaneous transluminal coronary angioplasty (PTCA) and coronary artery bypass graft. It will also be appreciated that the compounds may be useful in the treatment of other diseases mediated by binding of adhesion molecules to GPIIb/IIIa, for example cancer.

According to another aspect, therefore, the invention provides a method of inhibiting platelet aggregation in a warm-blooded mammal requiring such treatment, which comprises administering an effective amount of a compound of formula I, or a pharmaceutically acceptable metabolically labile ester or amide thereof, or a pharmaceutically acceptable salt thereof.

According to yet another aspect, the invention provides a method of inhibiting binding of fibrinogen to GPIIb/IIIa in a warm-blooded animal requiring such treatment, which comprises administering an effective amount of a compound of formula I, or a pharmaceutically acceptable metabolically labile ester or amide thereof, or a pharmaceutically acceptable salt thereof.

According to a further aspect, the invention provides the use of a compound of formula I, or a pharmaceutically acceptable metabolically labile ester or amide thereof, or a pharmaceutically acceptable salt thereof, for the manufacture of a medicament for the prevention or treatment of a disease involving platelet aggregation.

According to yet another aspect, the invention provides the use of a compound of formula I, or a pharmaceutically acceptable metabolically labile ester or amide thereof, or a pharmaceutically acceptable salt thereof, for the manufacture of a medicament for the prevention or treatment of a disease involving binding of fibrinogen to GPIIb/IIIa.

In general, a compound of formula I will be administered for this purpose by an oral, rectal, topical, intravenous, subcutaneous, intramuscular or inhalation route, so that a dose in the range of from 0.01 to 50 mg/kg body weight will be given, depending upon the route of administration, the age and sex of the patient, and the severity of the condition to be treated.

The compounds of formula I will generally be used in the form of a pharmaceutical composition comprising a compound of formula I, or a pharmaceutically acceptable metabolically labile ester or amide thereof, or a pharmaceutically acceptable salt thereof, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of creams or ointments or a transdermal (skin) patch for topical administration; in the form of a suppository for rectal administration in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation. Depending upon the route of administration, the composition will, in general, comprise, for example, 1 to 99% by weight of a compound of formula I.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The compounds according to the invention may be co-adminstrated or co-formulated with one or more agents known to be of value in diseases or conditions intended to be treated; for example a known platelet aggregation inhibitor (e.g. aspirin, a thromboxane antagonist or a thromboxane synthase inhibitor), hypolipidemic agent, anti-hypertensive agent, thrombolytic agent (such as streptokinase, urokinase, prourokinase, tissue plasminogen activator and derivatives thereof), beta-adrenergic blocker or a vasodilator may usefully also be present in a pharmaceutical composition of the invention for use in treating a heart or vascular disease or condition.

In addition to their use in therapeutic medicine, the compounds of formula I are also useful as pharmacological tools in the development and standardisation of test systems for the evaluation of the effects of adhesion molecules in laboratory animals such as cats, dogs, rabbits, monkeys, rats and mice, as part of the search for new therapeutic agents. The compounds of formula I may also be used because of their platelet aggregation inhibitory properties in helping to store blood and to maintain the viability of blood and blood vessels in warm-blooded animals (or parts thereof) undergoing artificial extracorporeal circulation, for example during limb or organ transplants. When used for this purpose a compound of formula I, or a pharmaceutically acceptable salt thereof, will generally be administered so that a steady state concentration in the range, for example, 0.1 to 10 mg per liter is achieved in the blood.

The invention will now be illustrated by the following non-limiting Examples in which unless otherwise stated:(i)

(i) concentrations and evaporations were carried out by rotary evaporation in vacuo;

(ii) operations were carried out at ambient temperature, that is in the range 18°–26° C.;

(iii) column chromatography was carried out on silica (Merck Art. 9385) available from E. Merck and Co., Darmstadt, Germany;

(iv) yields are given for illustration only and are not necessarily the maximum attainable by diligent process development;

(v) proton NMR spectra were normally determined at 200 MHz or 250 MHz in dimethylsulphoxide-$d_6$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; and (vi) ether refers to diethyl ether, THF to tetrahydrofuran and DMSO to dimethylsulphoxide.

EXAMPLE 1

Methyl 4-[3-(4-amidinobenzoyl)ureido]phenoxyacetate, acetate salt

Methyl 4-[3-(4-thiocarbamoylbenzoyl)ureido]phenoxyacetate (870 mg) was suspended in acetone (100 ml) and iodomethane (10 ml) was added. The stirred suspension was heated to 50° C. After 24 and 48 hours respectively, two further aliquots of iodomethane (10 ml+10 ml) were added whilst stirring at 50° C. was continued. Removal of the solvents in vacuo yielded methyl 4-[3-(4-(methylthio)carbonimidoylbenzoyl)ureido]phenoxyacetate as an orange-brown solid residue which was not purified further. The residue was suspended in methanol (40 ml) and heated to 45°–50° C. with stirring before a solution of ammonium acetate (1.54 g) in methanol (20 ml) was added. After stirring overnight at 45°–50° C., extra portions of methanol (10 ml) and ammonium acetate (0.77 g) were added and the reaction mixture was heated to 70° C. with stirring. After stirring for a further 24 hours at 70° C., the solvents were removed in vacuo to yield a pale yellow solid which was crystallised, with filtration, from boiling methanol to give the title compound (208 mg) as an off-white solid: NMR Spectrum (DMSO-$d_6$) 1.78 (3H, s), 3.71 (3H, s), 4.77 (2H, s), 6.93 (2H, d), 7.50 (2H, d), 7.91 (2H, d), 8.14 (2H d) 9.00–11.00 (3H br); Mass Spectrum m/Z 371 (M+H)$^+$; Elemental Analysis: calculated for $C_{18}H_{18}N_4O_5$. 1.0 $CH_3CO_2H$. 0.75 $H_2O$: C, 54.1%; H, 5.34%; N, 12.6%; found: C, 54.3%; H, 5.0%; N, 12.3%.

The necessary starting material was prepared as follows:

(a) Methyl 4-aminophenoxyacetate, hydrochloride salt (1.09 g), was dissolved, with warming, in acetonitrile (50 ml) containing diisopropylethylamine (0.86 ml). To this solution at ambient temperature was added gradually with stirring a solution of 4-cyanobenzoyl isocyanate (1 g, preparation described in Weikert, R. J. et al (1991), J. Med. Chem. 34, 1630) in acetonitrile (5 ml). The precipitated solid was crystallised from boiling acetonitrile to give methyl 4-[3-(4-cyanobenzoyl)ureido]phenoxyacetate (930 mg) as an off-white solid: m.p. 214°–217° C.; NMR Spectrum (DMSO-$d_6$) 3.70 (3H, s), 4.77 (2H, s), 6.94 (2H, d), 7.48 (2H, d), 8.02 (2H, d), 8.12 (2H, d), 10.49 (1H, s), 11.19 (1H, s); Mass Spectrum m/Z 354 (M+H)$^+$.

(b) A solution of the product of step (a) (850 mg) in pyridine (48 ml) and triethylamine (7 ml) was covered with a blanket of $H_2S$ gas and stirred at ambient temperature for 16 hours. The reaction mixture was evaporated to dryness and the residue was triturated with dry ether. The resultant solid was washed thoroughly with ether to give methyl 4-[3-(4-thiocarbamoylbenzoyl)ureido]phenoxyacetate (880 mg) as a yellow solid: NMR Spectrum (DMSO-$d_6$) 3.72 (3H, s), 4.78 (2H, s), 6.95 (2H, d), 7.48 (2H, m), 7.93 (2H, d), 8.06 (2H, d), 9.65 (1H, br s), 10.05 (1H, br s), 10.62 (1H, s).

EXAMPLE 2 t-Butyl 4-[3-(4-amidinobenzoyl)ureido]phenoxyacetate

In a similar manner to Example 1, t-butyl 4-[3-(4-thiocarbamoylbenzoyl)ureido]phenoxyacetate (4.4 g) was reacted with iodomethane (25 ml) and acetone (450 ml) and the resultant product was treated with ammonium acetate (10 g), methanol (400 ml) and dichloromethane (100 ml) at ambient temperature. This yielded a crude yellow solid (1.2 g), which was triturated with methanol, collected, washed with methanol and then stirred with 50% aqueous acetic acid solution (15 ml). Any solid material was filtered and discarded and the filtrate was evaporated and triturated under a mixture of ether and methanol to give the title compound (300 mg) as an off-white solid: NMR Spectrum (DMSO-$d_6$) 1.44 (9H, s), 1.77 (1.8H, s), 4.62 (2H, s), 6.90 (2H, d), 7.49 (2H, d), 7.92 (2H, d), 8.15 (2H, d), 9.50–10.4 (3H, br), 10.60 (1H s); Mass Spectrum m/Z 413 (M+H)$^+$; Elemental Analysis: calculated for $C_{21}H_{24}N_4O_5$. 0.6 $CH_3CO_2H$. 1.5 $H_2O$: C, 56.0%; H, 6.2%; N, 11.7%; found: C, 56.3%; H, 6.2%; N, 11.1%.

The necessary starting material was prepared as follows:

(a) A solution of benzyl chloroformate (14 ml) in THF (30 ml) was added dropwise over 40 minutes to an ice-cold solution of 4-aminophenol (11 g) in THF (500 ml), the temperature of the reaction mixture being maintained at 0°–5° C. On completion of the addition, the reaction mixture was stirred at ambient temperature for 2 hours and the precipitated solid was collected and crystallised from a mixture of ethyl acetate and hexane to give 4-benzyloxycarbonylaminophenol (11.3 g) as a white solid: m.p. 153°–154° C.; Elemental Analysis: calculated for $C_{14}H_{13}NO_3$: C, 69.1%; H, 5.4%; N, 5.8%; found: C, 69.3%; H, 5.3%; N, 5.8%.

(b) t-Butyl bromoacetate (15.5 ml) was added dropwise over 10 minutes to a mixture of the product of step (a) (21 g), anhydrous potassium carbonate (20 g) and acetone (450 ml). On completion of the addition the reaction mixture was stirred at ambient temperature overnight. Insoluble material was removed by filtration and the filtrate was evaporated to dryness. The solid residue was crystallised from ethyl acetate to give t-butyl 4-benzyloxycarbonylaminophenoxyacetate (25.1 g) as a white solid: m.p. 109°–110° C.; NMR Spectrum (DMSO-$d_6$) 1.42 (9H, s), 4.56 (2H, s), 5.12 (2H, s), 6.82 (2H, d), 7.31–7.43 (7H, m), 9.54 (1H, br s).

(c) To a solution of the product of step (b) (5 g) in ethanol (300 ml) containing glacial acetic acid (0.8 ml) under argon was added 10% Pd on C (250 mg). The argon was replaced by hydrogen and the reaction mixture was stirred under a blanket of hydrogen for 4 hours. The catalyst was filtered off through a pad of diatomaceous earth and washed with ethanol, and the combined filtrate and washings were evaporated to dryness to yield t-butyl 4-aminophenoxyacetate, acetate salt (2.5 g) as brown oil: NMR Spectrum (DMSO-$d_6$) 1.41 (9H, s), 1.86 (3H, s), 4.43 (2H, s), 5.12 (2H, s), 6.49 (2H, d), 6.60 (2H, m).

(d) In a similar manner to Example 1, starting material step (a), the product of step (c) (4.9 g), triethylamine (2.45 ml), 4-cyanobenzoyl isocyanate (3.1 g) and acetonitrile (600 ml) gave, after stirring at ambient temperature for 3 hours and storage at 10° C. overnight, t-butyl 4-[3-(4-cyanobenzoyl)ureido]phenoxyacetate (4.6 g) directly as a white solid: m.p. 208 ° C. (decomposes); NMR Spectrum (DMSO-$d_6$) 1.43 (9H, s), 4.62 (2H, s), 6.90 (2H, d), 7.48 (2H, m), 7.98 (2H, d), 8.13 (2H, d), 10.48 (1H, s), 11.19 (1H, s); Mass Spectrum m/Z 395 (M+H)$^+$; Elemental Analysis: calculated for $C_{21}H_{21}N_3O_5$: C, 63.8%; H, 5.4%; N, 10.6%; found: C, 63.7%; H, 5.5%; N, 10.6%.

(e) In a similar manner to Example 1, starting material step (b), the product of step (d) (3.5 g), pyridine (245 ml), triethylamine (38 ml) and $H_2S$ gas were reacted to give t-butyl 4-[3-(4-thiocarbamoylbenzoyl)ureido]phenoxyacetate (4.5 g) as a yellow solid: m.p. 248° C. (decomposes); NMR Spectrum (DMSO-$d_6$) 1.45 (9H, s), 4.62 (2H, s), 6.92 (2H, d), 7.49 (2H, d), 7.95 (2H, d), 8.05 (2H, d), 9.63 (1H, s), 10.05 (1H, s), 10.60 (1H, s), 11.05 (1H, s); Mass Spectrum m/Z 430 (M+H)$^+$.

EXAMPLE 3

4-[3-(4-Amidinobenzoyl)ureido]phenoxyacetic acid, trifluoroacetate salt

To a stirred suspension of the product of Example 2 (154 mg) in a mixture of dichloromethane (2 ml) and anisole (0.25 ml) was added trifluoroacetic acid (2.7 ml) at 0°–5° C. The resultant solution was stirred at that temperature for 20 minutes and at ambient temperature for 2.5 hours. The reaction mixture was evaporated and the residue was triturated with dry ether. The solid was collected and washed with ether to give the title compound (91 mg) as a pale yellow solid: NMR Spectrum (DMSO-$d_6$) 4.65 (2H, s), 6.92 (2H, d), 7.48 (2H, d), 7.93 (2H, d), 8.18 (2H, d), 9.31 (2H, br s), 9.45 (2H, br s), 10.54 (1H, s), 11.21 (1H, s); Mass Spectrum m/Z 413 (M+H)$^+$; Elemental Analysis: calculated for $C_{17}H_{16}N_4O_5$. 1.0 $CF_3CO_2H$: C, 48.5%; H, 3.6%; N, 11.9%; found: C, 48.5%; H, 3.7%; N, 11.8%.

EXAMPLE 4 t-Butyl 4-[3-(6-amidinopyrid-3-ylcarbonyl)ureido]phenoxyacetate, acetate salt In a similar manner to Example 1, t-butyl 4-[3-(6-thiocarbamoylpyrid-3-ylcarbonyl)ureido]phenoxyacetate (2.73 g) was reacted with iodomethane (13 ml) and acetone (200 ml) and the resultant product was treated with ammonium acetate (6 g), methanol (30 ml) and dichloromethane (30 ml) at ambient temperature. This yielded a crude solid which was collected and washed with methanol and acetone to give the title compound (1.68 g) as an orange solid: m.p. 290°–300° C. (decomposes); NMR Spectrum (DMSO-$d_6$) 1.43 (9H, s), 1.82 (3H, s), 4.62 (2H, s), 6.90 (2H, d), 7.49 (2H, d), 8.29 (1H, d), 8.52 (1H, dd), 9.18 (1H, d) 10.61 (1H, s); Mass Spectrum m/Z 414 (M+H)$^+$; Elemental Analysis: calculated for $C_{20}H_{23}N_5O_5$. 1.0 $CH_3CO_2H$. 0.5 $H_2O$: C, 54.8%; H, 5.85%; N, 14.5%; found: C, 54.6%; H, 6.0%; N, 14.5%

The necessary starting material was prepared as follows:

(a) To a stirred suspension of 6-cyanonicotinamide (Synthesis (1983), 316) (1.2 g) in 1,2-dichloroethane (28 ml) was added oxalyl chloride (1.3 ml) and the mixture was heated at reflux with stirring for 2.5 hours. The reaction mixture was cooled and the solvents were removed in vacuo to yield 6-cyanonicotinoyl isocyanate as a yellow solid residue. Then in a similar manner to Example 1, starting material step (a), this residue, t-butyl 4-aminophenoxyacetate, acetate salt (1.59 g), triethylamine (3.8 ml) and acetonitrile (140 ml total) gave, after stirring at ambient temperature for 3 hours followed by evaporation of the solvents, a yellow solid, which was collected, washed with cold acetonitrile and with hexane and dried to give t-butyl 4-[3-(6-cyanopyrid-3-yl-carbonyl)ureido]phenoxyacetate (2.37 g): m.p. 220°–222° C. (decomposes); NMR Spectrum (DMSO-$d_6$) 1.48 (9H, s), 4.67 (2H, s), 6.94 (2H, d), 7.52 (2H, d), 8.27 (1H, d), 8.58 (1H, dd), 9.25 (1H, d), 10.41 (1H, s), 11.40 (1H, s); Mass Spectrum m/Z 396 (M$^+$).

(b) In a similar manner to Example 1, starting material step (b), the product of step (a) (2.29 g), pyridine (105 ml), triethylamine (15 ml) and H$_2$S gas were reacted to give t-butyl 4-[3-(6-thiocarbamoylpyrid-3-ylcarbonyl)ureido] phenoxyacetate (2.76 g) as a yellow solid: m.p. 248°–249° C. (decomposes); NMR Spectrum (DMSO-$d_6$) 1.44 (9H, s), 4.62 (2H, s), 6.90 (2H, d), 7.49 (2H, d), 8.48 (1H, dd), 8.58 (1H, d), 9.10 (1H, d), 10.02 (1H, bs), 10.30 (1H, br s), 10.49 (1H, s), 11.30 (1H, s); Mass Spectrum m/Z 431 (M+H)$^+$.

EXAMPLE 5

4-[3-(6-Amidinopyrid-3-ylcarbonyl)ureido]phenoxyacetic acid, trifluoroacetate salt In a similar manner to Example 3, the product of Example 4 (300 mg) and trifluoroacetic acid (10 ml) were reacted to give the title compound (284 mg) as an orange solid: m.p. 270°–272° C. (decomposes); NMR Spectrum (DMSO-$d_6$) 4.65 (2H, s), 6.90 (2H, d), 7.49 (2H, d), 8.37 (1H, d), 8.65 (1H, dd), 9.26 (1H, d), 9.52 (2H, s), 9.65 (2H, s), 10.42 (1H, s), 11.40 (1H, s); Mass Spectrum m/Z 358 (M+H)$^+$; Elemental Analysis: calculated for $C_{16}H_{15}N_5O_5$. 1.0 CF$_3$CO$_2$H. 0.25 H$_2$O: C, 45.4%; H, 3.5%; N, 14.7%; found: C, 45.5%; H, 3.6%; N, 14.3%.

EXAMPLE 6 t-Butyl (2S)-2-(n-butylsulphonylamino)-3-[4-[3-(4-amidinobenzoyl)ureido]phenyl]propionate, acetate salt In a similar manner to Example 1, t-butyl (2S)-2-(n-butylsulphonylamino)-3-[4-[3-(4-thiocarbamoylbenzoyl)ureido]phenyl]propionate (2.4 g) was reacted with iodomethane (20 ml) and acetone (150 ml) and the resultant product was treated with ammonium acetate (4.4 g), methanol (50 ml) and dichloromethane (50 ml) at ambient temperature. This yielded a crude pale yellow solid (2.3 g), which was crystallised from hot isopropanol to give the title compound (1.35 g) as an off-white solid: NMR Spectrum (DMSO-$d_6$) 0.81 (3H, t), 1.06 (1.2H, d), 1.24 (2H, m), 1.39 (11H, m), 1.78 (3H, s), 2.71 (2H, m), 2.82 (1H, m), 2.98 (1H, m), 3.81 (0.2H, m), 3.99 (1H, m), 7.18 (2H, d), 7.54 (2H, d), 7.94 (2H, d), 8.15 (2H, d), 8.50–10.50 (2H, br), 10.87 (1H, br s); Mass Spectrum m/Z 546 (M+H)$^+$; Elemental Analysis: calculated for $C_{26}H_{35}N_5O_6S$. 1.0 CH$_3$CO$_2$H. 0.5 H$_2$O 0.2 (CH$_3$)$_2$CHOH: C, 54.8%; H, 6.69%; N, 11.2%; found: C, 54.8%; H, 6.8%; N, 11.0%.

The necessary starting material was prepared as follows:

(a) Liquid isobutylene (45 ml) was slowly added to a mixture of (2S)-2-amino-3-(4-nitrophenyl)propionic acid (7.2 g), 1,4-dioxane (45 ml) and concentrated sulphuric acid (4.5 ml) in a pressure bottle. The vessel was sealed and the reaction mixture was agitated at ambient temperature for 24 hours and then carefully opened. The excess of isobutylene was allowed to evaporate. The reaction mixture was poured into an ice-cold mixture of ethyl acetate (250 ml) and 0.25M NaOH(aq) (300–400 ml). The pH of the two-phase system was adjusted to between 9 and 10, and the ethyl acetate layer was separated. The aqueous layer was re-extracted with ethyl acetate (200 ml) and the combined organic extracts were washed with water, dried (MgSO$_4$) and evaporated to give t-butyl (2S)-2-amino-3-(4-nitrophenyl)propionate (6.9 g) as a brown oil which was used without further purification.

(b) To an ice-cold solution of the product of step (a) (6.9 g) and triethylamine (3.64 ml) in dichloromethane (100 ml) was added, with stirring, dropwise over 15 minutes a solution of butanesulphonyl chloride (4.1 g) in dichloromethane (10 ml). The reaction mixture was stirred at low temperature for 2 hours and then at ambient temperature for a further 2 hours. The solvents were removed in vacuo and the residue was partitioned between ethyl acetate (100 ml) and water (100 ml). The organic layer was separated and washed with water, dilute KHSO$_4$ (aq.), dilute NaHCO$_3$ (aq.), brine, dried (MgSO$_4$) and evaporated. The solid residue was collected and washed with hexane containing a small volume of ether to give t-butyl (2S)-2-(n-butylsulphonylamino)-3-(4-nitrophenyl)propionate (6.65 g) as an off-white solid: NMR Spectrum (CDCl$_3$) 0.90 (3H, t), 1.36 (2H, m), 1.45 (9H, s), 1.68 (2H, m), 2.88 (2H, m), 3.18 (2H, m), 4.28 (1H, m), 5.01 (1H, d), 7.43 (2H, d), 8.19 (2H, d).

(c) To a solution of the product of step (b) (2.9 g) and ammonium formate (1.90 g) in methanol (30 ml) under argon was added 10% Pd on C (450 mg). The reaction mixture was stirred at ambient temperature for 6 hours then the catalyst was filtered off using a pad of diatomaceous earth which was washed with methanol (30 ml). The combined filtrate and washings were evaporated to dryness and the residue was partitioned between ethyl acetate (50 ml) and dilute NaHCO$_3$ (aq.) (50 ml). The organic layer was separated, washed with water, dried (MgSO$_4$) and evaporated to yield a residue which slowly solidified to give t-butyl (2S)-2-(n-butylsulphonylamino)-3-(4-aminophenyl)propionate (2.59 g) as an off-white solid: NMR Spectrum (CDCl$_3$) 0.90 (3H, t), 1.36 (2H, m), 1.45 (9H, s), 1.67 (2H, m), 2.77 (2H, m), 2.93 (2H, m), 3.62 (2H, br s), 4.16 (1H, m), 4.68 (1H, d), 6.61 (2H, d), 6.99 (2H, d); Mass Spectrum m/Z 379 (M+Na)$^+$.

(d) In a similar manner to Example 1, starting material step (c), the product of step (c) (2.59 g) and 4-cyanobenzoyl isocyanate (1.29 g) in acetonitrile (100 ml total) were reacted to give, after stirring at ambient temperature for 1 hour and storage at 10° C. overnight, a solid, which was crystallised from isopropanol to give t-butyl (2S)-2-(n-butylsulphonylamino)-3-[4-[3-(4-cyanobenzoyl)ureido] phenyl]propionate (2.32 g) as a white solid: m.p. 171°–173° C.; NMR Spectrum (CDCl$_3$) 0.90 (3H, t), 1.37 (2H, m), 1.49 (9H, s), 1.73 (2H, m), 2.90 (2H, t), 3.11 (2H, m), 4.31 (1H, m), 5.61 (1H, d), 7.19 (2H, d), 7.42 (2H, d), 7.83 (2H, d), 8.19 (2H, d), 9.92 (1H, br s), 10.78 (1H, br s); Mass Spectrum m/Z 529 (M+H)$^+$.

(e) In a similar manner to Example 1, starting material step (b), the product of step (d) (2.32 g), pyridine (88 ml), triethylamine (13 ml) and H$_2$S gas were reacted to give t-butyl (2S)-2-(n-butylsulphonylamino)-3-[4-[3-(4-thiocarbamoylbenzoyl)ureido]phenyl]propionate (2.4 g) as a yellow solid: NMR Spectrum (DMSO-$d_6$) 0.79 (3H, t), 1.22 (2H, m), 1.38 (11H, m), 2.70 (2H, t), 2.79 (1H, m), 2.95 (1H, m), 3.95 (1H, m), 7.27 (2H, d), 7.53 (2H, d), 7.68 (1H, d), 7.96 (2H, d), 8.03 (2H, d), 9.66 (1H, br s), 10.05 (1H, br s), 10.74 (1H, s), 11.10 (1H, s); Mass Spectrum m/Z 563 (M+H)$^+$.

EXAMPLE 7

(2S)-2-(n-Butylsulphonylamino)-3-[4-[3-(4-amidinobenzoyl)ureido]phenyl]propionic acid, mixed trifluoroacetate and acetate salt In a similar manner to Example 3, t-butyl (2S)-2-(n-butylsulphonylamino)-3-[4-[3-(4-amidinobenzoyl)ureido]phenyl]propionate, acetate salt (100 mg), anisole (1 ml) and trifluoroacetic acid (9 ml) were reacted to give, after trituration with ether, a solid which was dissolved in 50% aqueous acetic acid (10 ml), washed with ether, filtered and lyophilised overnight to give the title mixture of compounds (65 mg) as a white solid: NMR Spectrum (DMSO-$d_6$) 0.80 (3H, t), 1.23 (2H, m), 1.45 (2H, m), 1.92 (0.9H, s), 2.72 (2H, m), 2.81 (1H, m), 3.04 (1H, m), 3.89 (0.2H, m), 7.05 (1H, br s), 7.28 (2H, d), 7.50 (2H, d), 7.94 (2H, d), 8.19 (2H, d), 8.60–10.70 (3H, br), 10.66 (1H s); Mass Spectrum m/Z 490 (M+H)$^+$; Elemental Analysis: calculated for $C_{22}H_{27}N_5O_6S$. 0.7 $CF_3CO_2H$. 0.3 $CH_3CO_2H$. 0.25 $H_2O$: C, 48.7%; H, 5.01%; N, 11.8%; found: C, 48.7%; H, 5.3%; N, 11.9%.

EXAMPLE 8 t-Butyl 4-[3-(4-amidinobenzoyl)ureido]-2-(t-butoxymethoxy)phenoxyacetate, acetate salt In a similar manner to Example 1, t-butyl 4-[3-(4-thiocarbamoylbenzoyl)ureido]-2-(t-butoxymethoxy)phenoxyacetate (2.4 g) was reacted with iodomethane (9 ml) and acetone (130 ml) and the resultant product was treated with ammonium acetate (5 g), methanol (150 ml) and dichloromethane (150 ml) at ambient temperature. This yielded a crude solid, which was triturated with methanol, collected, washed with ether, methanol and water, and dried under high vacuum to give the title compound (1.3 g) as an off-white solid: NMR Spectrum (DMSO-$d_6$) 1.44 (9H, s), 1.45 (9H, s), 1.77 (3H, s), 4.62 (2H, s), 4.67 (2H, s), 6.90 (1H, d), 7.09 (1H, dd), 7.29 (1H, d), 7.91 (2H, d), 8.12 (2H, d), 10.75 (1H, br s); Mass Spectrum m/Z 543 (M+H)$^+$; Elemental Analysis: calculated for $C_{27}H_{34}N_4O_8$. 1.0 $CH_3CO_2H$. 1.25 $H_2O$: C, 55.7%; H, 6.5%; N, 9.0%; found: C, 55.6%; H, 6.1%; N, 8.9%.

The necessary starting material was prepared as follows:

(a) In a similar manner to Example 2, starting material step (b), t-butyl bromoacetate (14 ml), 4-nitrocatechol (5 g), anhydrous potassium carbonate (14 g) and acetone (200 ml) gave, after crystallisation from ethyl acetate/hexane, 3,4-di-t-butoxycarbonylmethoxynitrobenzene (11.7 g) as an off-white solid: m.p. 90°–92° C.; NMR Spectrum (DMSO-$d_6$) 1.45 (18H, s), 4.83 (2H, s), 4.87 (2H, s), 7.10 (1H, d), 7.70 (1H, d), 7.92 (1H, dd); Elemental Analysis: calculated for $C_{18}H_{25}NO_8$: C, 56.4%; H, 6.6%; N, 3.7%; found: C, 56.2%; H, 6.5%; N, 3.6%.

(b) In a similar manner to Example 6, starting material step (c), the product of step (a) (1.1 g), ammonium formate (570 mg), methanol (30 ml) and 10% Pd on C (300 mg) gave 3,4-di-t-butoxycarbonylmethoxyaniline (850 mg) as a pale yellow oil: NMR Spectrum (DMSO-$d_6$) 1.45 (18H, s), 4.43 (2H, s), 4.53 (2H, s), 4.73 (2H, s), 6.07 (1H, dd), 6.15 (1H, d), 6.65 (1H, dd); Mass Spectrum m/Z 376 (M+Na)$^+$.

(c) In a similar manner to Example 1, starting material step (a), the product of step (b) (2.55 g), 4-cyanobenzoyl isocyanate (1.1 g) and acetonitrile (150 ml total) gave, after stirring at ambient temperature for 1 hour and storage at 10° C. overnight, a solid, which was crystallised from methanol/ethyl acetate to give t-butyl 4-[3-(4-cyanobenzoyl)ureido]-2-(t-butoxymethoxy)phenoxyacetate (2.38 g) as a white solid: m.p. 161°–162° C.; NMR Spectrum (DMSO-$d_6$) 1.46 (18H, s), 4.62 (2H, s), 4.68 (2H, s), 6.90 (1H, d), 7.09 (1H, dd), 7.26 (1H, d), 8.00 (2H, d), 8.15 (2H, d), 10.50 (1H, s), 11.2 (1H, s); Mass Spectrum m/Z 548 (M+Na)$^+$.

(d) In a similar manner to Example 1, starting material step (b), the product of step (c) (2.2 g), pyridine (186 ml), triethylamine (26 ml) and $H_2S$ gas were reacted to give t-butyl 4-[3-(4-thiocarbamoylbenzoyl)ureido]-2-(t-butoxymethoxy)phenoxyacetate (2.6 g) as a yellow solid: m.p. 198°–199° C.; NMR Spectrum (DMSO-$d_6$) 1.43 (9H, s), 1.44 (9H, s), 4.61 (2H, s), 4.66 (2H, s), 6.89 (1H, d), 7.09 (1H, dd), 7.27 (1H, d), 7.98 (4H, m), 9.68 (1H, s), 10.02 (1H, s), 10.66 (1H, s), 11.07 (1H, s); Mass Spectrum m/Z 582 (M+Na)$^+$.

EXAMPLE 9

4-[3-(4-Amidinobenzoyl)ureido]-2-(carboxymethoxy)phenoxyacetate

In a similar manner to Example 3, the product of Example 8 (300 mg) and trifluoroacetic acid (5 ml) were reacted to give the title compound (140 mg) as a pale yellow solid: NMR Spectrum (DMSO-$d_6$+$CF_3CO_2H$) 4.71 (2H, s), 4.76 (2H, s), 6.95 (1H, d), 7.18 (1H, dd), 7.32 (1H, d), 7.98 (2H, d), 8.27 (2H, d), 9.08 (2H, br s), 9.49 (2H, br s); Mass Spectrum m/Z 431 (M+H)$^+$; Elemental Analysis: calculated for $C_{19}H_{18}N_4O_8$. 0.2 $CF_3CO_2H$. 0.5 $H_2O$: C, 50.4%; H, 4.2%; N, 12.1%; found: C, 50.3%; H, 4.1%, N, 11.8%.

EXAMPLE 10 t-Butyl 4-[3-(4-amidinobenzoyl)ureido]-2-fluorophenoxyacetate, trifluoroacetate salt In a similar manner to Example 1, t-butyl 4-[3-(4-thiocarbamoylbenzoyl)ureido]-2-fluorophenoxyacetate (509 mg) was reacted with iodomethane (3.2 ml) and acetone (40 ml) at ambient temperature and the resultant product was treated with ammonium acetate (682 mg), methanol (12 ml) and dichloromethane (12 ml) also at ambient temperature. This yielded an off-white solid, which, after washing with ether, was purified using a reversed-phase silica column and an acetonitrile/water mobile phase containing 0.1% trifluoroacetic acid, to give, after lyophilisation, the title compound (50 mg) as a white fluffy solid: NMR Spectrum (DMSO-$d_6$) 1.44 (9H, s), 4.73 (2H, s), 7.08 (1H, t), 7.27 (1H, m), 7.62 (1H, dd), 7.92 (2H, d), 8.19 (2H, d), 9.22 (2H, br s), 9.47 (2H, brs), 10.63 (1H, s), 11.28 (1H, s); Mass Spectrum m/Z 431 (M+H)$^+$; Elemental Analysis: calculated for $C_{21}H_{23}FN_4O_5$. 1.0 $CF_3CO_2H$. 0.5 $H_2O$: C, 49.9%; H, 4.55%; N, 10.1%; found: C, 49.8%; H, 4.4%; N, 10.1%.

The necessary starting material was prepared as follows:

(a) In a similar manner to Example 2, starting material step (b), t-butyl bromoacetate (5.6 ml), 2-fluoro-4-nitrophenol (5 g), anhydrous potassium carbonate (5.3 g) and acetone (200 ml) were reacted to give t-butyl 2-fluoro-4-nitrophenoxyacetate (8.3 g) as an off-white solid: m.p. 62°–64° C.; NMR Spectrum (DMSO-$d_6$) 1.49 (9H, s), 4.70 (2H, s), 6.94 (1H, m), 8.01 (2H, m); Mass Spectrum m/Z 272 (M+H)$^+$.

(b) In a similar manner to Example 6, starting material step (c), the product of step (a) (8 g), ammonium formate (6.58 g), methanol (300 ml) and 10% Pd on C (3 g) were reacted to give as a yellow oil (6.5 g) t-butyl 4-amino-2- fluorophenoxyacetate: Mass Spectrum m/Z 241 (M)$^+$; 264 (M+Na)$^+$.

(c) In a similar manner to Example 1, starting material step (a), the product of step (b) (1.65 g), 4-cyanobenzoyl isocyanate (1.18 g) and acetonitrile (130 ml) were reacted after stirring at ambient temperature for 1 hour and storage at 10° C. overnight, to give a solid, which was crystallised twice from methanol/ethyl acetate to give t-butyl 4-[3-(4-cyanobenzoyl)ureido]-2'-fluorophenoxyacetate (504 mg): m/Z 413 (M)$^+$; 436 (M+Na)$^+$.

(d) In a similar manner to Example 1, starting material step (b), the product of step (c) (504 mg), pyridine (35 ml), triethylamine (5 ml) and H$_2$S gas were reacted to give t-butyl 4-[3-(4-thiocarbamoylbenzoyl)ureido]-2-fluorophenoxyacetate (509 mg): m/Z 447 (M)$^+$; 460 (M+Na)$^+$.

EXAMPLE 11 t-Butyl 4-[3-(4-amidinobenzoyl)ureido]-3-methylphenoxyacetate, trifluoroacetate salt In a similar manner to Example 1, t-butyl 4-[3-(4-thiocarbamoylbenzoyl)ureido]-3-methylphenoxyacetate (670 mg) was reacted with iodomethane (2.8 ml) and acetone (80 ml) at ambient temperature and the resultant product was treated with ammonium acetate, methanol (70 ml) and dichloromethane (25 ml) also at ambient temperature. This yielded an off-white solid, which, after washing with ether, was purified using reversed-phase silica chromatography and an acetonitrile/water mobile phase containing 0.1% trifluoroacetic acid to give, after lyophilisation and precipitation from methanol/ether, the title compound (150 mg) as a white fluffy solid: NMR Spectrum (DMSO-d$_6$) 1.46 (9H, s), 2.27 (3H, s), 4.63 (2H, s), 6.74 (1H, dd), 6.83 (1H, d), 7.73 (1H, d), 7.92 (2H, d), 8.20 (2H, d), 9.23 (2H, br s), 9.47 (2H, br s), 10.48 (1H, s), 11.30 (1H, s); Mass Spectrum m/Z 447 (M+H)$^+$; Elemental Analysis: calculated for C$_{22}$H$_{26}$N$_4$O$_5$. 1.3 CF$_3$CO$_2$H: C, 51.4%; H, 4.79%; N, 9.75%; found: C, 51.2%; H, 4.7%; N, 9.8%.

The necessary starting material was prepared as follows:

(a) In a similar manner to Example 2, starting material step (b), t-butyl bromoacetate (2.9 ml), 3-methyl-4-nitrophenol (2.5 g), anhydrous potassium carbonate (2.7 g) and acetone (100 ml) were reacted to give t-butyl 3-methyl-4-nitrophenoxyacetate (4.19 g) as an off-white solid: NMR Spectrum (DMSO-d$_6$) 1.44 (9H, s), 2.56 (3H, s), 4.71 (2H, s), 6.94 (1H, dd), 7.03 (1H, d), 8.06 (1H, d); Mass Spectrum m/Z 268 (M+H)$^+$.

(b) To a solution of the product from step (a) (4.18 g) in methanol (250 ml) under argon was added p-toluenesulphonic acid monohydrate (2.99 g) followed by 10% Pd on C (1.8 g). The argon was replaced by hydrogen and the reaction mixture was stirred under a blanket of hydrogen for 6 hours. The catalyst was filtered off through a pad of diatomaceous earth and washed with methanol. The blue-coloured filtrate and washings were evaporated to near dryness and excess ether was added. On storage overnight at −10° C. a solid crystallised which was collected, washed with ether and dried to give t-butyl 4-amino-3-methylphenoxyacetate, p-toluenesulphonate salt (2.93 g) as an off-white solid: NMR Spectrum (DMSO-d$_6$) 1.42 (9H, s), 2.28 (3H, s), 2.30 (3H, s), 4.63 (2H, s), 6.82 (1H, dd), 6.88 (1H, d), 7.12 (2H, d), 7.24 (1H, d), 7.48 (2H, d), 9.50 (3H, br s); Mass Spectrum m/Z 260 (M+Na)$^+$.

(c) In a similar manner to Example 1, starting material step (a), the product of step (b) (2.9 g), 4-cyanobenzoyl isocyanate (1.23 g), diisopropylethylamine (1.23 ml) and acetonitrile (125 ml total) were reacted to give, after stirring at ambient temperature overnight, a solid, which was crystallised from acetonitrile/ether to give t-butyl 4-[3-(4-cyanobenzoyl)ureido]-3-methylphenoxyacetate (611 mg) as an off-white solid: NMR Spectrum (DMSO-d$_6$) 1.44 (9H, s), 2.27 (3H, s), 4.61 (2H, s), 6.73 (1H, dd), 6.81 (1H, d), 7.72 (1H, d), 8.00 (2H, d), 8.13 (2H, d), 10.41 (1H, s), 11.23 (1H, s); Mass Spectrum m/Z 432 (M+Na)$^+$.

(d) In a similar manner to Example 1, starting material step (b), the product of step (c) (611 mg), pyridine (70 ml), triethylamine (10 ml) and H$_2$S gas were reacted to give t-butyl 4-[3-(4-thiocarbamoylbenzoyl)ureido]-3-methylphenoxyacetate (660 mg) as a yellow solid: NMR Spectrum (DMSO-d$_6$) 1.44 (9H, s), 2.27 (3H, s), 4.61 (2H, s), 6.76 (1H, dd), 6.83 (1H, d), 7.76 (1H, d), 7.95 (2H, d), 8.05 (2H, d), 9.67 (1H, br s), 10.06 (1H, br s), 10.55 (1H, s), 11.12 (1H, s); Mass Spectrum m/Z 466 (M+Na)$^+$.

EXAMPLE 12

Isopropyl 4-[3-(4-amidinobenzoyl)ureido]-3-methylphenoxyacetate, acetate salt

In a similar manner to Example 1, isopropyl 4-[3-(4-thiocarbamoylbenzoyl)ureido]-3-methylphenoxyacetate (12.23 g) was reacted with iodomethane (100 ml) and acetone (750 ml) at ambient temperature and the resultant product was treated with ammonium acetate (15.4 g), methanol (350 ml) and dichloromethane (300 ml) at ambient temperature for 3 days and then at reflux for 5 hours. The mixture was filtered whilst hot, diluted with ether to turbidity and stored overnight at 10° C. to give a solid which was collected, washed with methanol/dichloromethane/ether, 1:1:2 (100 ml) and with ether and dried to give the title compound (7.88 g) as a pale yellow solid: NMR Spectrum (DMSO-d$_6$) 1.23 (6H, d), 2.28 (3H, s), 4.71 (2H, s), 5.01 (1H, m), 6.77 (1H, dd), 6.86 (1H, d), 7.78 (1H, d), 7.91 (2H, d), 8.15 (2H, d), 10.55 (1H, br s); Elemental Analysis: calculated for C$_{21}$H$_{24}$N$_4$O$_5$. 1.0 CH$_3$CO$_2$H. 0.21H$_2$O: C, 58.0%; H, 6.01%; N, 11.8%; found: C, 57.4%; H, 6.1%; N, 11.5%.

The necessary starting material was prepared as follows:

(a) In a similar manner to Example 2, starting material step (b), isopropyl bromoacetate (13.9 ml), 3-methyl-4-nitrophenol (15 g), anhydrous potassium carbonate (16.25 g) and acetone (500 ml) were reacted to give isopropyl 3-methyl-4-nitrophenoxyacetate (22.2 g) as an off-white solid: NMR Spectrum (DMSO-d$_6$) 1.22 (6H, d), 2.54 (3H, s), 4.89 (2H, s), 5.00 (1H, m), 6.96 (1H, dd), 7.04 (1H, d), 8.03 (1H, d); Mass Spectrum m/Z 254 (M+H)$^+$.

(b) In a similar manner to Example 11, starting material step (b), the product from step (a) (14.35 g), ethyl acetate (60 ml), isopropanol (500 ml), p-toluenesulphonic acid monohydrate (11.41 g) and platinum oxide catalyst (400 mg) under hydrogen gave, after 30 hours, a purple-coloured oil, which, on re-dissolving in a small volume of isopropanol and diluting with ether, followed by storage at 10° C., gave a solid which was collected, washed with ether and dried. There was thus obtained isopropyl 4-amino-3-methylphenoxyacetate, p-toluenesulphonate salt (15.75 g) as an off-white solid: m.p. 119°–121° C.; NMR Spectrum (DMSO-d$_6$) 1.21 (6H, d), 2.27 (3H, s), 2.29 (3H, s), 4.74 (2H, s), 4.98 (1H, m), 6.84 (1H, dd), 6.93 (1H, d), 7.12 (2H, d), 7.25 (1H, d), 7.48 (2H, d), 9.60 (3H, br s); Mass Spectrum m/Z 224 (M+H)$^+$.

(c) In a similar manner to Example 1, starting material step (a), the product of step (b) (15 g), 4-cyanobenzoyl isocyanate (6.3 g), diisopropylethylamine (8 ml) and acetonitrile (400 ml total) were reacted to give, after stirring at ambient temperature for 1.5 hours and storage overnight at 10° C., a solid, which was collected, washed with acetonitrile/ether, 3:1, and ether. The material was recrystallised from acetonitrile to give isopropyl 4-[3-(4-cyanobenzoyl)ureido]-3-methylphenoxyacetate (11.36 g) as an off-white solid: m.p. 233°–234° C.; NMR Spectrum (DMSO-d$_6$) 1.23 (6H, d), 2.26 (3H, s), 4.69 (2H, s), 5.00 (1H, m), 6.78 (1H, dd), 6.84 (1H, d), 7.75 (1H, d), 8.01 (2H, d), 8.13 (2H, d), 10.42 (1H, s), 11.26 (1H, s); Mass Spectrum m/Z 418 (M+Na)$^+$.

(d) In a similar manner to Example 1, starting material step (b), the product of step (c) (11.36 g), pyridine (500 ml), triethylamine (70 ml) and H$_2$S gas were reacted to give isopropyl 4-[3-(4-thiocarbamoylbenzoyl)ureido]-3-methylphenoxyacetate (12.23 g) as a yellow solid: NMR Spectrum (DMSO-d$_6$) 1.24 (6H, d), 2.28 (3H, s), 4.69 (2H, s), 5.01 (1H, m), 6.78 (1H, dd), 6.85 (1H, d), 7.77 (1H, d), 7.96 (2H, d), 8.05 (2H, d), 9.65 (1H, br s), 10.04 (1H, br s), 10.56 (1H, s), 11.11 (1H, s); Mass Spectrum m/Z 452 (M+Na)$^+$.

EXAMPLE 13

Isopropyl 4-[3-(4-amidinobenzoyl)ureido]-3-methylphenoxyacetate, hydrochloride salt A mixture of isopropyl 4-[3-(4-amidinobenzoyl)ureido]-3-methylphenoxyacetate, acetate salt (5 g), and methanol (250 ml) was heated to reflux before a solution of pyridine hydrochloride (1.34 g) in methanol (50 ml) was added. The resultant mixture was heated to reflux until all the solids had dissolved. The hot solution was diluted with isopropanol (100 ml), quickly filtered, and the filtrate was again diluted with isopropanol (100 ml). On storage overnight at 10° C., a solid precipitated which was collected, washed with isopropanol/ether, 1:1, and ether, and dried to give the title compound (4.17 g) as an off-white solid: m.p. 257°–258° C.; NMR Spectrum (DMSO-d$_6$) 1.23 (3H, s), 2.27 (3H, s), 4.70 (2H, s), 5.00 (1H, m), 6.79 (1H, dd), 6.87 (1H, d), 7.75 (1H, d), 7.95 (2H, d), 8.21 (2H, d), 9.30 (2H, br s), 9.54 (2H, br s), 10.48 (1H, s), 11.29 (1H, s); Mass Spectrum m/Z 413 (M+H)$^+$; Elemental Analysis: calculated for C$_{21}$H$_{24}$N$_4$O$_5$. 1.0 HCl. 0.02 H$_2$O: C, 56.1%; H, 5.62%, N, 12.5%; found: C, 55.8%; H, 5.5%; 12.3%.

EXAMPLE 14

4-[3-(4-Amidinobenzoyl)ureido]-3-methylphenoxyacetic acid

A mixture of isopropyl 4-[3-(4-amidinobenzoyl)ureido]-3-methylphenoxyacetate, acetate salt (500 mg), water (50 ml), 50% aqueous acetic acid (1.5 ml) and 2N HCl (1.5 ml) was stirred and heated to 90°–100° C. until all the solids had dissolved. The hot solution was then quickly filtered and the filtrate was heated to 80°–85° C. and stored at that temperature for 3 days. The mixture was cooled and the solid was collected, washed thoroughly with water, methanol and with ether. The solid was suspended in refluxing methanol/dichloromethane, 4:1 (50 ml). The insoluble material was collected, washed with hot methanol and with ether and dried to give the title compound (250 mg), as a pale yellow solid: NMR Spectrum (DMSO-d$_6$+CF$_3$CO$_2$H) 2.30 (3H, s), 4.66 (2H, s), 6.81 (1H, dd), 6.89 (1H, d), 7.78 (1H, d), 7.97 (2H, d), 8.24 (2H, d), 9.17 (2H, br s), 9.48 (2H, br s), 10.51 (1H, s), 11.25 (1H, s); m/Z 371 (M+H)$^+$; Elemental Analysis: calculated for C$_{18}$H$_{18}$N$_4$O$_5$. 1.25 H$_2$O: C, 55.0%; H, 5.26%; N, 14.3%; found: C, 54.9%; H, 5.3%; N, 14.2%.

EXAMPLE 15

Ethyl 4-[3-(4-amidinobenzoyl)ureido]phenoxyacetate, acetate salt

In a similar manner to Example 1, ethyl 4-[3-(4-thiocarbamoylbenzoyl)ureido]phenoxyacetate (11 g) was reacted with iodomethane (110 ml) and acetone (1000 ml) at ambient temperature and the resultant product was treated with ammonium acetate (14 g), ethanol (400 ml) and dichloromethane (300 ml). This yielded a pale yellow solid, which, after washing with dichloromethane/ethanol, 9:1, dichloromethane and ether, yielded a solid (6.2 g) which was recrystallised from boiling ethanol/acetonitrile to give the title compound (3.3 g) as a pale yellow solid: m.p.>300° C. (decomposes); NMR Spectrum (CD$_3$CO$_2$D) 1.28 (3H, t), 4.27 (2H, q), 4.69 (2H, s), 6.96 (2H, d), 7.51 (2H, d), 8.05 (2H, d), 8.25 (2H, d); Mass Spectrum m/Z 385 (M+H)$^+$; Elemental Analysis: calculated for C$_{19}$H$_{20}$N$_4$O$_5$. 1.0 CH$_3$CO$_2$H. 0.5 H$_2$O: C, 55.6%; H, 5.56%; N, 12.4%; found: C, 55.8%; H, 5.3%; N, 12.1%.

The necessary starting material was prepared as follows:

(a) In a similar manner to Example 1, starting material step (a), the p-toluenesulphonate salt of ethyl 4-aminophenoxyacetate (12.9 g, preparation described by Coutts, I. G. C. et al (1985), J. Chem. Soc. Perkin I, 1829), 4-cyanobenzoyl isocyanate (5.9 g), acetonitrile (400 ml total) and diisopropylethylamine (6.5 ml) were reacted to give, after stirring at ambient temperature for 1.5 hours, a solid, which was crystallised from acetonitrile/ethanol to give ethyl 4-[3-(4-cyanobenzoyl)ureido]phenoxyacetate (10.16 g) as an off-white solid: m.p. 200°–203° C.; NMR Spectrum (DMSO-d$_6$) 1.22 (3H, t), 4.17 (2H, q), 4.75 (2H, s), 6.93 (2H, d), 7.49 (2H, d), 8.02 (2H, d), 8.13 (2H, d), 10.49 (1H, br s), 11.17 (1H, br s); Mass Spectrum m/Z 368 (M+H)$^+$.

(b) In a similar manner to Example, starting material step 1 (b), the product of step (a) (10.12 g), pyridine (500 ml), triethylamine (80 ml) and H$_2$S gas were reacted to give ethyl 4-[3-(4-thiocarbamoylbenzoyl)ureido]phenoxyacetate (11 g) as a yellow solid: NMR Spectrum (DMSO-d$_6$) 1.21 (3H, t), 4.18 (2H, q), 4.74 (2H, s), 6.93 (2H, d), 7.49 (2H, d), 7.95 (2H, d), 8.03 (2H, d), 9.64 (1H, br s), 10.03 (1H, br s), 10.60 (1H, s), 11.04 (1H, s); Mass Spectrum m/Z 402 (M+H)$^+$.

EXAMPLE 16

Ethyl 4-[3-(4-amidinobenzoyl)ureido]phenoxyacetate, hemicitrate salt

To a suspension of ethyl 4-[3-(4-amidinobenzoyl)ureido]phenoxyacetate, acetate salt (100 mg), in methanol (5 ml) was added a solution of citric acid monohydrate (47 mg) in methanol (1 ml). The resultant mixture was sonicated for 5 minutes and then heated to boiling. The resultant solution was filtered hot. On cooling to 10° C., a solid precipitated which was collected, washed with methanol and ether, and dried to give the title compound (57 mg) as a white crystalline solid: m.p. 198°–200° C. (decomposes); NMR Spectrum (DMSO-$d_6$) 1.23 (3H, t), 2.41 (2H, q), 4.18 (2H, q), 4.77 (2H, s), 6.94 (2H, d), 7.50 (2H, d), 7.94 (2H, d), 8.18 (2H, d), 10.30 (4H, br s), 10.60 (1H, s); Elemental Analysis: calculated for $C_{19}H_{20}N_4O_5$. 0.5 $C_6H_8O_7$. 0.33 $H_2O$: C, 54.3%; H, 5.11%; N, 11.5%; found: C, 54.5%; H, 5.1%; N, 11.4%.

EXAMPLE 17

Ethyl 4-[3-(4-amidinobenzoyl)ureido]phenoxyacetate, hydrochloride salt

To a suspension of ethyl 4-[3-(4-amidinobenzoyl)ureido] phenoxyacetate, acetate salt (1.3 g), in methanol (60 ml) was added a solution of pyridine hydrochloride (400 mg) in methanol (5 ml). The resultant mixture was sonicated for 5 minutes and then heated to boiling. The resultant solution was filtered hot and diluted to turbidity with ether. On cooling to 10° C., a solid precipitated which was collected, washed with ether and recrystallised from methanol/ether to give the title compound (500 mg) as an off-white crystalline solid: m.p. 246°–250° C. (decomposes); NMR Spectrum (DMSO-$d_6$) 1.23 (3H, t), 4.18 (2H, q), 4.76 (2H, s), 6.95 (2H, d), 7.50 (2H, d), 7.96 (2H, d), 8.20 (2H, d), 9.28 (2H, br s), 9.53 (2H, br s), 10.58 (1H, s), 11.22 (1H, s); Mass Spectrum m/Z 385 (M+H)$^+$; Elemental Analysis: calculated for $C_{19}H_{20}N_4O_5$. 1.0 HCl: C, 54.2%; H, 5.03%; N, 13.3%; found: C, 54.4%; H, 4.9%; N, 13.3%.

EXAMPLE 18

Isopropyl 4-[3-(4-amidinobenzoyl)ureido]phenoxyacetate, acetate salt

In a similar manner to Example 1, isopropyl 4-[3-(4-thiocarbamoylbenzoyl)ureido]phenoxyacetate (10.88 g) was reacted with iodomethane (60 ml) and acetone (600 ml) at ambient temperature and the resultant product was treated with ammonium acetate (12 g), methanol (220 ml) and dichloromethane (220 ml). This yielded, after filtering the reaction mixture whilst hot and evaporating the filtrate to near dryness, a pale yellow solid, which was slurried in dichloromethane and stirred at ambient temperature overnight, filtered and the solid dissolved in hot methanol. After cooling, the precipitated solid was collected and washed with dichloromethane to give the title compound (2.4 g) as a pale yellow solid: m.p. >300° C. (decomposes); NMR Spectrum (DMSO-$d_6$) 1.29 (6H, d), 4.77 (2H, s), 5.06 (1H, m), 6.97 (2H, d), 7.54 (2H, d), 7.97 (2H, d), 8.20 (2H, d), 10.75 (1H, br s); Mass Spectrum m/Z 399 (M+H)$^+$; Elemental Analysis: calculated for $C_{20}H_{22}N_4O_5$. 1.0 $CH_3CO_2H$. 0.5 $H_2O$: C, 56.5%; H, 5.8%; N, 12.0%; found: C, 56.7%; H, 5.9%; N, 11.9%.

The necessary starting material was prepared as follows:

(a) In a similar manner to Example 11, starting material step (b), isopropyl 4-nitrophenoxyacetate (19.1 g, preparation described in Mahajan R. K. et al (1985), Coll. Czech. Chem. Commun. 50, 690), ethyl acetate (300 ml), isopropanol (300 ml), p-toluenesulphonic acid monohydrate (15.2 g) and platinum oxide catalyst (400 mg) was stirred under hydrogen for 24 hours to give an oil. This material was dissolved in a small volume of isopropanol, diluted with ether at 10° C. to give a solid which was collected, washed with ether and dried. There was thus obtained isopropyl 4-aminophenoxyacetate, p-toluenesulphonate salt (22 g), as an off-white solid: m.p.135°–137° C.; NMR Spectrum (DMSO-$d_6$) 1.21 (6H, d), 2.29 (3H, s), 4.77 (2H, s), 4.98 (1H, m), 7.02 (2H, d), 7.11 (2H, d), 7.27 (2H, d), 7.48 (2H, d), 9.70 (3H, br s); Mass Spectrum m/Z 210 (M+H)$^+$.

(b) In a similar manner to Example 1, starting material step (a), the product from step (a) (15 g), 4-cyanobenzoyl isocyanate (6.8 g), acetonitrile (400 ml total) and diisopropylethylamine (9 ml) were reacted to give a solid which was collected and washed thoroughly with acetonitrile. There was thus obtained isopropyl 4-[3-(4-cyanobenzoyl)ureido] phenoxyacetate (11.3 g) as an off-white solid: m.p. 190°–201° C.; NMR Spectrum (DMSO-$d_6$) 1.22 (6H, d), 4.71 (2H, s), 5.00 (1H, m), 6.92 (2H, d), 7.49 (2H, d), 8.02 (2H, d), 8.13 (2H, d), 10.49 (1H, s), 11.19 (1H, br s); Mass Spectrum m/Z 382 (M+H)$^+$; Elemental Analysis: calculated for $C_{20}H_{19}N_3O_5$: C, 63.0%; H, 5.02%; N, 11.0%; found: C, 62.9%; H, 4.9%; N, 11.1%.

(c) In a similar manner to Example 1, starting material step (b), the product of step (b) (11.3 g), pyridine (490 ml), triethylamine (70 ml) and $H_2S$ gas were reacted to give isopropyl 4-[3-(4-thiocarbamoylbenzoyl)ureido]phenoxyacetate (10.88 g) as a yellow solid: m.p. 224°–227° C. (decomposes); NMR Spectrum (DMSO-$d_6$) 1.23 (6H, d), 4.72 (2H, s), 5.01 (1H, m), 6.92 (2H, d), 7.50 (2H, d), 7.95 (2H, d), 8.04 (2H, d), 9.67 (1H, br s), 10.05 (1H, br s), 10.62 (1H, s), 11.05 (1H, s); Mass Spectrum m/Z 416 (M+H)$^+$.

EXAMPLE 19

3-(4-[3-(4-Amidinobenzoyl)ureido]phenyl)-2-(2-ethoxyethyl)propionic acid, trifluoroacetate salt In a similar manner to Example 3, t-butyl 3-(4-[3-(4-amidinobenzoyl)ureido]phenyl)-2-(2-ethoxyethyl)propionate, acetate salt (82 mg), and trifluoroacetic acid (5 ml) were reacted to give the title compound (64 mg) as an off-white solid: NMR Spectrum (DMSO-$d_6$) 1.08 (3H, t), 1.70 (2H, m), 2.73 (3H, m), 3.35 (4H, m), 7.19 (2H, d), 7.48 (2H, d), 7.92 (2H, d), 8.18 (21H, d), 9.35 (4H, br s), 10.64 (1H, s), 11.25 (1H, br s), 12.05 (1H, br s); Mass Spectrum m/Z 427 (M+H)$^+$; Elemental Analysis: calculated for $C_{22}H_{26}N_4O_5$. 1.4 $CF_3CO_2H$: C, 50.8%; H, 4.7%; N, 9.6%; found: C, 50.6%; H, 4.8%; N, 9.8%.

The necessary starting material was prepared as follows:

(a) A 55% dispersion of sodium hydride in mineral oil (5.46 g) was added by portions to a solution of di-t-butyl malonate (25.8 g) in t-butanol (100 ml) under argon. The reaction mixture was stirred at ambient temperature for 1 hour before sodium iodide (1.53 g) and 2-ethoxyethyl chloride (13.1 ml) were added. The resultant mixture was heated to reflux for 48 hours and then evaporated to dryness. The residue was partitioned between water and ether, the organic layer was separated, washed with brine, dried (MgSO$_4$) and evaporated. The resultant oily residue was purified by flash chromatography on silica by elution with 10% ethyl acetate/ hexane to give t-butyl 2-t-butoxycarbonyl-4-ethoxybutyrate (21 g) as a colourless oil: NMR Spectrum (CDCl$_3$) 1.19 (3H, t), 1.45 (18H, s), 2.07 (2H, m), 3.34 (1H, t), 3.45 (4H, m); Mass Spectrum m/Z 289 (M+H)$^+$.

(b) To a solution of the product from step (a) (5 g) in dioxane (25 ml) was added a solution of potassium hydroxide (1 g) in water (20 ml). The cloudy reaction mixture was heated to reflux for 5.5 hours and then evaporated to dryness. The residue was dissolved in water, washed with ether, and acidified to pH 4 with conc. HCl. The mixture was extracted thoroughly with ethyl acetate and the combined extracts were washed with brine, dried (MgSO$_4$) and evaporated to give 2-t-butoxycarbonyl-4-ethoxybutyric acid (1.06 g) as a yellow oil: NMR Spectrum (CDCl$_3$) 1.19 (3H, t), 1.49 (9H, s), 2.19 (2H, m), 3.50 (5H, m); Mass Spectrum m/Z 233 (M+H)$^+$.

(c) To a solution of cyclohexylisopropylamine (1.42 ml) in dry THF (3 ml) at −76° C. under argon was added a 2.5M solution of n-butyllithium in hexane (3.5 ml). The resultant solution was stirred at −76° C. for 15 minutes before a solution of the product from step (b) (1 g) in dry THF (7 ml) was added dropwise. On completion of the addition, the reaction mixture was allowed to warm to 0° C. and stirred at that temperature for 15 minutes before a solution of 4-nitrobenzyl bromide (940 mg) in dry THF (3 ml) was added, followed by 1,3-dimethyl-3,4,5,6-tetrahydro-2(1H)-pyrimidinone (1.5 ml). The resultant mixture was stirred at ambient temperature for 16 hours and then heated to reflux for 5 hours. The reaction mixture was evaporated to dryness and saturated ammonium chloride solution was added to the residue. The resultant mixture was extracted thoroughly with ethyl acetate and the combined extracts were washed with brine, dried (MgSO$_4$) and evaporated to give a residue which was purified by flash chromatography on silica by elution with 20% ethyl acetate/hexane to give t-butyl 2-(2-ethoxyethyl)-3-(4-nitrophenyl)propionate (940 mg) as a pale yellow oil: NMR Spectrum (CDCl$_3$) 1.19 (3H, t), 1.33 (9H, s), 1.76 (1H, m), 1.94 (1H, m), 2.78 (1H, m), 2.91 (2H, m), 3.44 (4H, m), 7.35 (2H, d), 8.13 (2H, d); Mass Spectrum m/Z 324 (M+H)$^+$.

(d) In a similar manner to Example 11, starting material step (b), the product from step (c) (887 mg), methanol (10 ml), p-toluenesulphonic acid monohydrate (520 mg) and platinum oxide catalyst (50 mg) were reacted under hydrogen to give, after 5 hours, t-butyl 3-(4-aminophenyl)-2-(2-ethoxyethyl)propionate, p-toluenesulphonate salt (1.26 g), as an off-white solid: m.p. 129°–134° C.; NMR Spectrum (DMSO-d$_6$+CD$_3$CO$_2$D) 1.10 (3H, t), 1.30 (9H, s), 1.71 (2H, m), 2.32 (3H, s), 2.64 (1H, m), 2.70 (2H, m), 3.37 (4H, m), 7.15 (2H, d), 7.30 (4H, m), 7.56 (2H, d); Mass Spectrum m/Z 294 (M+H)$^+$.

(e) In a similar manner to Example 1, starting material step (a), the product from step (d) (1.2 g), 4-cyanobenzoyl isocyanate (450 mg), acetonitrile (30 ml) and diisopropylethylamine (0.59 ml) were reacted to give, after stirring at ambient temperature for 4 hours, a mixture, which was diluted dropwise with water (30 ml). The resultant precipitated solid was collected, washed thoroughly with water and dried to give t-butyl 3-(4-[3-(4-cyanobenzoyl)ureido]phenyl)-2-(2-ethoxyethyl)propionate (624 mg) as an off-white solid: m.p. 144°–145° C.; NMR Spectrum (DMSO-d$_6$) 1.10 (3H, t), 1.30 (9H, s), 1.70 (2H, m), 2.60 (1H, m), 2.72 (2H, m), 3.35 (4H, m), 7.14 (2H, d), 7.49 (2H, d), 8.01 (2H, d), 8.13 (2H, d), 10.48 (1H, s), 11.20 (1H, s); Mass Spectrum m/Z 466 (M+H)$^+$.

(f) In a similar manner to Example 1, starting material step (b), the product of step (e) (600 mg), pyridine (42 ml), triethylamine (6 ml) and H$_2$S gas were reacted to give t-butyl 2-(2-ethoxyethyl)-3-(4-[3-(4-thiocarbamoylbenzoyl)ureido]phenyl)propionate (585 mg) as a yellow solid: m.p. 199°–201° C.; NMR Spectrum (DMSO-d$_6$) 1.10 (3H, t), 1.30 (9H, s), 1.70 (2H, m), 2.62 (1H, m), 2.72 (2H, m), 3.37 (4H, m), 7.15 (2H, d), 7.49 (2H, d), 7.95 (2H, d), 8.03 (2H, d), 9.67 (1H, br s), 10.06 (1H, br s), 10.72 (1H, s), 11.09 (1H, s); Mass Spectrum m/Z 522 (M+H)$^+$.

(g) In a similar manner to Example 1, the product of step (f) (570 mg) was reacted with iodomethane (5 ml) and acetone (50 ml) at ambient temperature and the resultant product was treated with ammonium acetate (1 g), methanol (7 ml) and dichloromethane (5 ml). There was thus obtained a solid (600 mg) which was slurried in a small volume of methanol, filtered, washed with a little methanol and with ether, and dried. There was thus obtained t-butyl 3-(4-[3-(4-amidinobenzoyl)ureido]phenyl)-2-(2-ethoxyethyl)propionate, acetate salt (100 mg), as a white solid: m.p.>300° C.; NMR Spectrum (DMSO-d$_6$) 1.09 (3H, t), 1.30 (9H, s), 1.70 (2H, m), 1.79 (3H, s), 2.61 (1H, m), 2.72 (2H, m), 3.35 (4H, m), 7.14 (2H, d), 7.50 (2H, d), 7.92 (2H, d), 8.15 (2H, d), 10.80 (1H, br s); Mass Spectrum m/Z 483 (M+H)$^+$; Elemental Analysis: calculated for C$_{26}$H$_{34}$N$_4$O$_5$. 1.0 CH$_3$CO$_2$H. 1.5 H$_2$O: C, 59.0%; H, 7.25%; N, 9.8%; found: C, 58.9%; H, 7.3%; N, 9.9%.

EXAMPLE 20

N-[N-(4-Amidinobenzoyl)carbamoyl]piperidin-4-yloxyacetic acid, trifluoroacetate salt Ethyl N-[N-(4-Amidinobenzoyl)carbamoyl]piperidin-4-yloxyacetate, acetate salt (100 mg), was dissolved in a 1% (by volume) solution of triethylamine (4 ml) in water and the resultant mixture was stirred at ambient temperature overnight. Glacial acetic acid (0.6 ml) was added and the mixture was filtered. The filtrate was purified directly using reversed-phase column chromatography on silica in a similar manner to that used in Example 10. There was thus obtained the title compound (21 mg) as a white foam: NMR Spectrum (DMSO-d6) 1.50 (2H, m), 1.88 (2H, m), 3.25 (2H, m), 3.67 (3H, m), 4.06 (2H, s), 7.90 (2H, d), 8.00 (2H, d), 9.10 (2H, br s), 9.40 (2H, br s), 10.41 (1H, s), 12.55 (1H, br s); Mass Spectrum m/Z 349 (M+H)$^+$; 371 (M+Na)$^+$.

The necessary starting material was prepared as follows:

(a) To a mixture of N-benzyloxycarbonyl-4-hydroxypiperidine (2.4 g, preparation described by Alig, L. et al (1992), J. Med. Chem. 35, 4393), dirhodium tetraacetate (40 mg) and dichloromethane (15 ml) under argon was added dropwise over 3–4 hours, with stirring, a solution of ethyl diazoacetate (1.2 ml) in dichloromethane (2.5 ml). On completion of the addition, the reaction mixture was stirred at ambient temperature overnight and then evaporated. The resultant oily residue was purified by column chromatography on silica eluting with 30% ethyl acetate/hexane to give ethyl N-(benzyloxycarbonyl)piperidin-4-yloxyacetate (2.4 g) as a colourless oil: NMR Spectrum (CDCl$_3$) 1.20 (3H, t), 1.40 (2H, m), 1.82 (2H, m), 3.13 (2H, m), 3.57 (1H, m), 3.70 (2H, m), 4.11 (2H, q), 4.13 (2H, s), 5.07 (2H, s), 7.35 (5H, m); Mass Spectrum m/Z 322 (M+H)$^+$.

(b) In a similar manner to Example 2, starting material step (c), the product from step (a) (2.3 g), ethanol (200 ml), glacial acetic acid (0.6 ml), 10% Pd on C (200 mg) and hydrogen gas were reacted to give ethyl piperidin-4-yloxyacetate, acetate salt (1.7 g), as a brown oil: NMR Spectrum (DMSO-d$_6$) 1.20 (3H, t), 1.41 (2H, m), 1.82 (3H, s), 1.86 (2H, m), 2.58 (2H, m), 2.95 (2H, m), 3.46 (1H, m), 4.11 (4H, m); Mass Spectrum m/Z 188 (M+H)$^+$.

(c) In a similar manner to Example 1, starting material step (a), the product from step (b) (1.7 g), 4-cyanobenzoyl isocyanate (1.1 g), acetonitrile (100 ml total) and triethylamine (2.1 ml) were stirred at ambient temperature overnight. The mixture was evaporated and the residue was purified by column chromatography on silica eluting with 5% ethanol/dichloromethane to give ethyl N-[N-(4-cyanobenzoyl)carbamoyl]piperidin-4-yloxyacetate (1.24 g) as a pale yellow oil: NMR Spectrum (DMSO-$d_6$) 1.21 (3H, t), 1.50 (2H, m), 1.87 (2H, m), 3.20 (2H, m), 3.67 (3H, m), 4.12 (2H, q), 4.15 (2H, s), 7.97 (4H, s), 10.40 (1H, br s); Mass Spectrum m/Z 360 (M+H)$^+$.

(d) In a similar manner to Example 1, starting material step (b), the product from step (c) (1.2 g), pyridine (84 ml), triethylamine (7 ml) and H$_2$S gas were reacted to give ethyl N-[N-(4-thiocarbamoylbenzoyl)carbamoyl]piperidin-4-yloxyacetate (0.74 g) as a yellow gum: NMR Spectrum (DMSO-$d_6$) 1.20 (3H, t), 1.50 (2H, m), 1.87 (2H, m), 3.20 (2H, m), 3.66 (3H, m), 4.12 (2H, q), 4.15 (2H, s), 7.90 (4H, m), 9.63 (1H, br s), 10.00 (1H, br s); Mass Spectrum m/Z 394 (M+H)$^+$.

(e) In a similar manner to Example 1, the product of step (d) (740 mg), iodomethane (4 ml) and acetone (100 ml) were reacted at ambient temperature and the product so obtained was treated with ammonium acetate (1.4 g), ethanol (120 ml) and dichloromethane (60 ml). This yielded an oily residue which was dissolved in ethanol (5 ml) and dichloromethane (20 ml). This mixture was centrifuged to remove a fine precipitate and the supernatant was decanted and evaporated to yield an off-white gum (600 mg) which was not purified further but contained predominantly ethyl N-[N-(4-amidinobenzoyl)carbamoyl]piperidin-4-yloxyacetate, acetate salt, NMR Spectrum (DMSO-$d_6$+CD$_3$CO$_2$D) 1.14 (3H, t), 1.50 (2H, m), 1.84 (5H, m), 3.18 (2H, m), 3.64 (3H, m), 4.05 (2H, q), 4.07 (2H, s), 7.83 (2H, d), 7.96 (2H, d); Mass Spectrum m/Z 377 (M+H)$^+$, 399 (M +Na)$^+$.

EXAMPLE 21

N-[N-(4-Amidinobenzoyl)carbamoyl]piperidin-4-ylmethoxyacetic acid, trifluoroacetate salt In a similar manner to Example 20, ethyl N-[N-(4-amidinobenzoyl)carbamoyl]piperidin-4-ylmethoxyacetate (210 mg) and 1% aqueous triethylamine (8.4 ml) were reacted with stirring for 28 hours to give the title compound (25 mg) as a white foam: NMR Spectrum (DMSO-$d_6$+CD$_3$CO$_2$D) 1.25 (2H, m), 1.80 (3H, m), 2.93 (2H, m), 3.37 (2H, d), 4.01 (4H, m), 7.91 (2H d), 8.02 (2H d); Mass Spectrum m/Z 363 (M+H)$^+$; Elemental Analysis: calculated for C$_{17}$H$_{22}$N$_4$O$_5$. 1.00 CF$_3$CO$_2$H. 1.5 H$_2$O: C, 45.3%; H, 5.2%; N, 11.1%; found: C, 45.7%; H, 5.2%; N, 11.1%.

The necessary starting material was prepared as follows:

(a) In a similar manner to Example 20, starting material step (a), N-benzyloxycarbonylpiperidine-4-methanol (2 g, preparation described in Turconi, M. et al (1989), European Patent Application No. 309422-A2), dirhodium tetraacetate (40 mg), dichloromethane (15 ml total) and ethyl diazoacetate (1.2 ml) were reacted to give ethyl N-(benzyloxycarbonyl)piperidin-4-ylmethoxyacetate (1.47 g) as a colourless oil: NMR Spectrum (DMSO-$d_6$) 1.10 (2H, m), 1.20 (3H, t), 1.70 (3H, m), 2.80 (2H, m), 3.31 (2H, d), 4.00 (2H, m), 4.06 (2H, s), 4.12 (2H, q), 5.06 (2H, s), 7.35 (5H, m); Mass Spectrum m/Z 336 (M+H)$^+$.

(b) In a similar manner to Example 2, starting material step (c), the product from step (a) (1.4 g), ethanol (100 ml), glacial acetic acid (0.25 g), 10% Pd on C (140 mg) and hydrogen gas were reacted to give ethyl piperidin-4-ylmethoxyacetate, acetate salt (1.1 g), as a brown oil: NMR Spectrum (DMSO-$d_6$) 1.12 (2H, m), 1.20 (3H, t), 1.62 (3H, m), 1.84 (3H, s), 2.48 (2H, m), 2.96 (2H, m), 3.29 (2H, d), 4.05 (2H, s), 4.12 (2H, q).

(c) In a similar manner to Example 1, starting material step (a), the product from step (b) (1.1 g), 4-cyanobenzoyl isocyanate (720 mg), acetonitrile (90 ml total) and triethylamine (1.2 ml) were reacted to give, after stirring at ambient temperature overnight and evaporation, a residue, which was purified directly by column chromatography on silica eluting with 30% ethyl acetate/hexane. There was thus obtained ethyl N-[N-(4-cyanobenzoyl)carbamoyl]piperidin-4-ylmethoxyacetate (420 mg) as an off-white gum: NMR Spectrum (DMSO-$d_6$); 1.21 (5H, m), 1.71 (2H, m), 1.82 (1H, m), 2.90 (2H, m), 3.34 (2H, d), 4.00 (2H, m), 4.08 (2H, s), 4.13 (2H, q), 7.98 (4H, s), 10.40 (1H, br s); Mass Spectrum m/Z 374 (M+H)$^+$.

(d) In a similar manner to Example 1, starting material step (b), the product from step (c) (400 mg), pyridine (28 ml), triethylamine (4 ml) and H$_2$S gas were reacted to give ethyl N-[N-(4-thiocarbamoylbenzoyl)carbamoyl]piperidin-4-ylmethoxyacetate (340 mg) as a yellow solid: NMR Spectrum (DMSO-$d_6$) 1.20 (5H, m), 1.72 (2H, m), 1.82 (1H, m), 2.89 (2H, m), 3.34 (2H, d), 3.95 (2H, m), 4.08 (2H, s), 4.12 (2H, q), 7.89 (4H, m), 9.61 (1H, br s), 10.00 (1H, br s); Mass Spectrum m/Z 408 (M+H)$^+$.

(e) In a similar manner to Example 1, the product from step (d) (380 mg), iodomethane (2 ml) and acetone (40 ml) were reacted at ambient temperature and the product so obtained was reacted with ammonium acetate (800 mg), ethanol (40 ml) and dichloromethane (20 ml). This yielded an oily residue which was purified by column chromatography on silica eluting with 10% ethanol/dichloromethane to give ethyl N-[N-(4-amidinobenzoyl)carbamoyl]piperidin-4-ylmethoxyacetate (210 mg) which was used without further purification.

EXAMPLE 22

Illustrative pharmaceutical dosage forms suitable for presenting the compounds of the invention for therapeutic or prophylactic use include the following, which may be obtained by conventional procedures well known in the art.

| a) Tablet I | mg/tablet |
|---|---|
| Active ingredient | 1.0 |
| Lactose Ph. Eur. | 93.25 |
| Croscarmellose sodium | 4.0 |
| Maize starch paste (5% w/v aqueous paste) | 0.75 |

| b) Tablet II | mg/tablet |
|---|---|
| Active ingredient | 50 |
| Lactose | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| c) Tablet III | mg/tablet |
|---|---|
| Active ingredient | 100 |
| Lactose | 182.75 |
| Croscarmellose sodium | 12.0 |
| Maize starch paste (5% w/v aqueous paste) | 2.25 |
| Magnesium stearate | 3.0 |

| (d) Capsule | mg/capsule |
|---|---|
| Active ingredient | 10 |
| Lactose Ph. Eur. | 488.5 |
| Magnesium stearate | 1.5 |

-continued

| (e) Injection | mg/ml |
|---|---|
| Active ingredient (acid addition salt) | 1.0 |
| Sodium chloride | 9.0 |
| Purified water to 1.0 ml | |

CHEMICAL FORMULAE $R^1-CON(R^2)-CON(R^3)-X^1-Q-X^2-G$     I

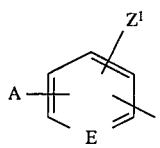     II

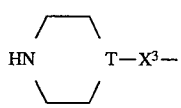     III

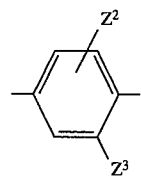     IV

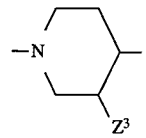     V $R^1-CON(R^2)-CON(R^3)-X^1-Q-X^2-COOG^1$     VI

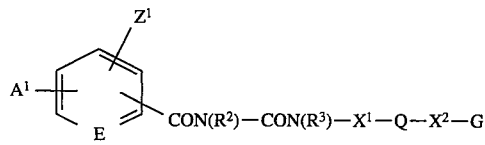     VII

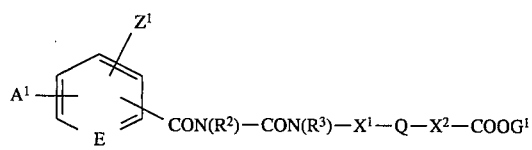     VIII $R^1CO-NCO$     IX $H_2N-X^1-Q-X^2-G$     X $R^1-CON(R^2)-CON(R^3)-X^1-Q-X^{2a}-G$     XI $R^4X-U^1$     XII

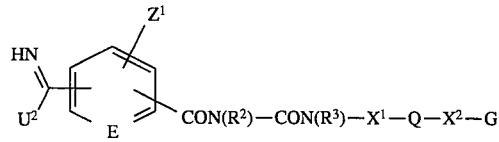     XIII $H_2N-X^1-Q-X^2-COOG^1$     XIV

-continued
CHEMICAL FORMULAE

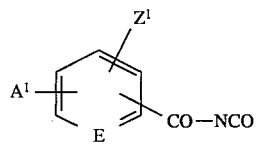     XV $R^1-CONH_2$     XVI

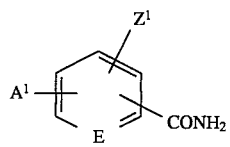     XVII $H_2N-X^1-Q-X^{2a}-G$     XVIII

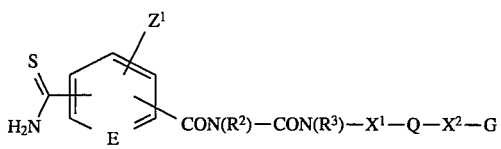     XIX

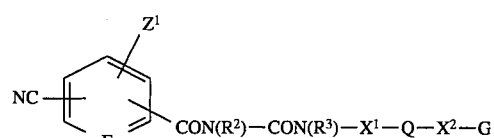     XX

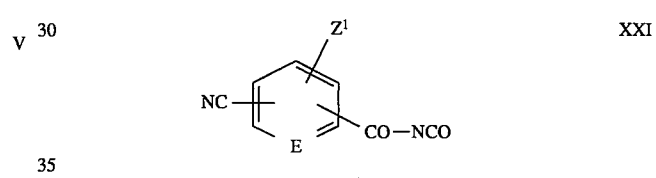     XXI

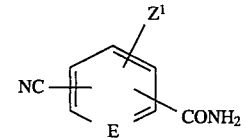     XXII

We claim:

1. A compound of formula I $R^1-CON(R^2)-CON(R^3)-X^1-Q-X^2-G$     I wherein $R^1$ represents a group of formula II

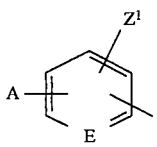     II in which A is attached meta or para to the position where the group $CONR^2CONR^3$ is attached and is selected from guanidino and $R^aN=C(NH_2)$— where $R^a$ is hydrogen or phenyl which is unsubstituted or substituted by 1 or 2 of halogeno, (1–4C)alkyl, (1–4C)alkoxy, cyano and nitro, E is CH or N, and $Z^1$ is hydrogen, halogeno, (1–4C)alkyl, (1–4C)alkoxy;

$R^2$ and $R^3$ which may be the same or different represent hydrogen (1–4C)alkyl or ar(1–4C)alkyl;

$X^1$ is a bond or (1–4C)alkylene, provided that when Q is a group of formula V, $X^1$ is not methylene;

Q is a group of formula IV or V

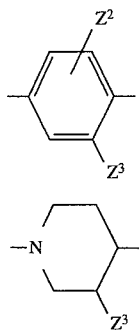

in which $Z^2$ is hydrogen, halogeno, (1–4C)alkyl, (1–4C)alkoxy, cyano or nitro, and $Z^3$ is a group of formula $X^2$—$G^a$ in which $X^2$ can have any of the values given hereinafter for $X^2$ and $G^a$ can have any of the values given hereinafter for G, or $G^a$ has any of the values given hereinbefore for $Z^2$;

or the partial structure of formula $NR^3X^1Q$ is a group of formula V in which $Z^3$ can have any of the values given hereinbefore for $Z^3$;

$X^2$ is a bond, (1–4C)alkylene, oxy(1–3C)alkylene, (1–3C)alkylene-oxy(1–3C)alkylene or a group of formula $CH_2CH(NHXR^4)$ in which X is $SO_2$, CO or $CO_2$ and $R^4$ is (1–6C)alkyl, (6–12C)aryl or (6–12C)aryl(1–4C)alkyl in which any aryl group is optionally substituted by (1–4C)alkyl, or $X^2$ is a group of formula $CH_2CH(CH_2CH_2O(1-4C)alkyl)$; and G is a carboxy group or a pharmaceutically acceptable metabolically labile ester or amide thereof;

or a pharmaceutically acceptable salt thereof.

2. A chemical compound of formula I as claimed in claim 1 wherein $R^1$ represents a group of formula II in which A is attached meta or para to the position where the group $CONR^2CONR^3$ is attached and is selected from guanidino and $R^aN=C(NH_2)$— where $R^a$ is hydrogen or phenyl which is unsubstituted or substituted by 1 or 2 of halogeno, (1–4C)alkyl, (1–4C)alkoxy, cyano and nitro, E is CH or N, and $Z^1$ is hydrogen, halogeno, (1–4C)alkyl, (1–4C)alkoxy;

$R^2$ and $R^3$ which may be the same or different represent hydrogen, (1–4C)alkyl or ar(1–4C)alkyl;

$X^1$ is a bond or (1–4C)alkylene, provided that when Q is a group of formula V, $X^1$ is not methylene;

Q is a group of formula IV or V in which $Z^2$ is hydrogen, halogeno, (1–4C)alkyl, (1–4C)alkoxy, cyano or nitro, and $Z^3$ is a group of formula $X^2$—$G^a$ in which $G^a$ can have any of the values given for G, or has any of the values given for $Z^2$;

$X^2$ is a bond, (1–4C)alkylene, oxy(1–3C)alkylene or a group of formula $CH_2CH(NHXR^4)$ in which X is $SO_2$, CO or $CO_2$ and $R^4$ is (1–6C)alkyl, (6–12C)aryl or (6–12C)aryl(1–4C)alkyl in which any aryl group is optionally substituted by (1–4C)alkyl; and G is a carboxy group or a pharmaceutically acceptable metabolically labile ester or amide thereof;

or a pharmaceutically acceptable salt thereof.

3. A compound of formula I as claimed in claim 1 wherein $R^1$ represents a group of formula II in which A is attached para to the position where the group $CONR^2CONR^3$ is attached and is a group of formula $R^aN=C(NH_2)$— where $R^a$ is hydrogen or phenyl, E is CH or N and $Z^1$ is hydrogen, fluoro, chloro, methyl or methoxy;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula $X^2$—$G^a$ in which $X^2$ is oxymethylene and $G^a$ is carboxy, methoxycarbonyl, ethoxycarbonyl, propoxycarbonyl, isopropoxycarbonyl or t-butoxycarbonyl;

$X^2$ is ethylene, trimethylene, oxymethylene, methyleneoxymethylene, a group of formula $CH_2CH(NHSO_2(CH_2)_3CH_3)$ or a group of formula $CH_2CH(CH_2CH_2OCH_2CH_3)$; and G is carboxy, methoxycarbonyl, ethoxycarbonyl, propoxycarbonyl, isopropoxycarbonyl or t-butoxycarbonyl;

or a pharmaceutically-acceptable salt thereof.

4. A compound of formula I as claimed in claim 1 wherein $R^1$ represents a group of formula II in which A is attached para to the position where the group $CONR^2$ is attached and is a group of formula $R^aN=C(NH_2)$— where $R^a$ is hydrogen or phenyl, E is CH or N and $Z^1$ is hydrogen, fluoro, chloro, methyl or methoxy;

$R^2$ is hydrogen, methyl or benzyl;

the partial structure of formula $NR^3X^1Q$ is a group of formula V in which $Z^3$ is hydrogen or a group of formula $X^2$—$G^a$ in which $X^2$ is oxymethylene and $G^a$ is carboxy, methoxycarbonyl, ethoxycarbonyl, propoxycarbonyl, isopropoxycarbonyl or t-butoxycarbonyl;

$X^2$ is ethylene, trimethylene, oxymethylene or methyleneoxymethylene; and

G is carboxy, methoxycarbonyl, ethoxycarbonyl, propoxycarbonyl, isopropoxycarbonyl or t-butoxycarbonyl;

or a pharmaceutically acceptable salt thereof.

5. A compound of formula I as claimed in claim 1 wherein $R^1$ represents a group of formula II in which A is attached para to the position where the group $CONR^2$ is attached and is a group of formula $R^aN=C(NH_2)$— where $R^a$ is hydrogen, E is CH and $Z^1$ is hydrogen;

$R^2$ is hydrogen;

the partial structure of formula $NR^3X^1Q$ is a group of formula V in which $Z^3$ is hydrogen;

$X^2$ is oxymethylene or methyleneoxymethylene; and

G is carboxy, methoxycarbonyl, ethoxycarbonyl, propoxycarbonyl, isopropoxycarbonyl or t-butoxycarbonyl;

or a pharmaceutically acceptable salt thereof.

6. A compound of formula I as claimed in claim 1 selected from:

methyl 4-[3-(4-amidinobenzoyl)ureido]phenoxyacetate, t-butyl 4-[3-(4-amidinobenzoyl)ureido]phenoxyacetate, 4-[3-(4-amidinobenzoyl)ureido]phenoxyacetic acid, ethyl 4-[3-(4-amidinobenzoyl)ureido]phenoxyacetate, isopropyl 4-[3-(4-amidinobenzoyl)ureido]phenoxyacetate, N-[N-(4-amidinobenzoyl)carbamoyl]piperidin-4-yloxyacetic acid and N-[N-(4-amidinobenzoyl)carbamoyl]piperidin-4-yl-methoxyacetic acid;
or a pharmaceutically acceptable salt thereof.

7. A compound of the formula I

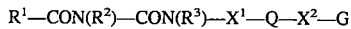   I wherein $R^1$ represents a group of formula II

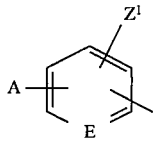   II in which A is attached para to the position where the group $CONR^2CONR^3$ is attached and is a group of formula $R^aN\!=\!C(NH_2)$— where $R^a$ is hydrogen;

E is CH and $Z^1$ is hydrogen;

$R^2$ is hydrogen;

$R^3$ is hydrogen or methyl;

$X^1$ is a bond;

Q is a group of formula IV

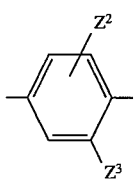   IV in which $Z^2$ is hydrogen, fluoro, chloro or methyl, and $Z^3$ is hydrogen or a group of formula $X^2$—$G^a$ in which $X^2$ is oxymethylene and $G^a$ is carboxy, methoxycarbonyl, ethoxycarbonyl, propoxycarbonyl, isopropoxycarbonyl or t-butoxycarbonyl;

$X^2$ is oxymethylene; and

G is carboxy, methoxycarbonyl, ethoxycarbonyl, propoxycarbonyl, isopropoxycarbonyl or t-butoxycarbonyl;

or a pharmaceutically acceptable salt thereof.

8. A compound of formula I

   I wherein $R^1$ represents a group of formula II

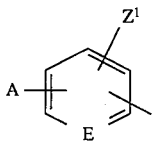   II in which A is attached para to the position where the group $CONR^2CONR^3$ is attached and is a group of formula $R^aN\!=\!C(NH_2)$— where $R^a$ is hydrogen or phenyl;

E is CH or N;

$Z^1$ is hydrogen, fluoro, chloro, methyl, methoxy or cyano;

$R^2$ and $R^3$, which may be the same or different, represent hydrogen, (1–4C)alkyl or ar(1–4C)alkyl;

$X^1$ is a bond or (1–4C)alkylene;

Q is a group of formula IV

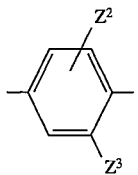   IV in which $Z^2$ is hydrogen, fluoro, chloro, methyl, methoxy or cyano, and $Z^3$ is hydrogen, or a group of formula $X^2$—$G^a$ in which $X^2$ is methylene, ethylene or oxymethylene, and G and $G^a$, which may be the same or different, represents a carboxy group or a pharmaceutically acceptable metabolically labile ester thereof;

or a pharmaceutically acceptable salt thereof.

9. A process for the preparation of a compound of formula I

   I or a pharmaceutically acceptable metabolically labile ester or amide thereof, or a pharmaceutically acceptable salt thereof, as claimed in any one of claims 1–3, 4, 5–6, 7 and 8 which comprises:

(A) for a compound of formula I in which G is carboxy, deprotecting a compound of formula VI

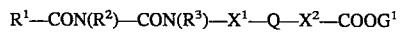   VI in which $G^1$ is a carboxy protecting group;

(B) for a compound of formula I in which $R^1$ is a group of formula II

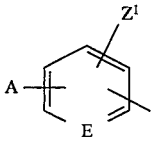   II and A is an amidino group, deprotecting a compound of formula VII

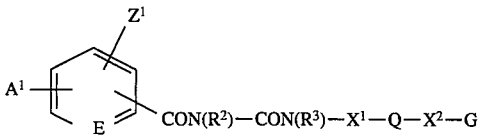   VII in which $A^1$ is a protected amidino group;

(C) for a compound of formula I in which $R^2$ and $R^3$ represent hydrogen atoms, reacting an isocyanate of formula IX

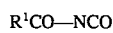   IX with an amine of formula X

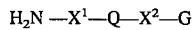   X (D) for a compound of formula I in which $X^2$ is a group of formula $CH_2CH(NHXR^4)$, reacting a compound of formula XI

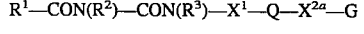   XI in which $X^{2a}$ is $CH_2CH(NH_2)$, or an acid addition salt thereof, with a compound of formula XII

   XII in which $U^1$ is a leaving atom or group; or (E) for a compound of formula I in which $R^1$ is a group of formula II and A is a group of formula $R^aN=C(NH_2)-$, reacting a compound of formula XIII

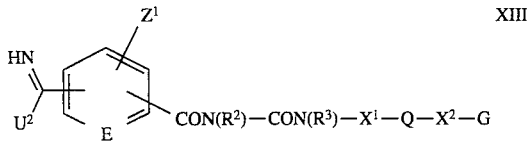

XIII in which $U^2$ is a leaving atom or group, with a compound of formula $R^aNH_2$, or an acid addition salt thereof;

whereafter a compound of formula I optionally may be converted into a pharmaceutically acceptable metabolically labile ester or amide thereof, or a pharmaceutically acceptable salt thereof.

10. A pharmaceutical composition comprising a compound of formula I, or a pharmaceutically acceptable metabolically labile ester or amide thereof, or a pharmaceutically acceptable salt thereof, as claimed in any one of claims 1–3, 4, 5–6, 7 and 8 together with a pharmaceutically acceptable diluent or carrier.

11. A method of inhibiting platelet aggregation in a warm-blooded mammal in need thereof comprising administering to such mammal a platelet aggregation inhibiting amount of a compound of formula I as claimed in any one of claims 1–3, 4, 5–6, 7 and 8.

* * * * *